United States Patent
Koval et al.

(10) Patent No.: US 10,919,934 B2
(45) Date of Patent: Feb. 16, 2021

(54) COMPOSITIONS AND METHODS FOR MANAGING RESPIRATORY CONDITIONS

(71) Applicant: Emory University, Atlanta, GA (US)

(72) Inventors: Michael Koval, Atlanta, GA (US); Barbara Schlingmann, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/922,564

(22) Filed: Jul. 7, 2020

(65) Prior Publication Data

US 2020/0331965 A1 Oct. 22, 2020

Related U.S. Application Data

(62) Division of application No. 15/953,133, filed on Apr. 13, 2018, now Pat. No. 10,738,079.

(60) Provisional application No. 62/485,552, filed on Apr. 14, 2017.

(51) Int. Cl.
| | |
|---|---|
| *C07K 7/06* | (2006.01) |
| *A61K 45/06* | (2006.01) |
| *A61K 31/166* | (2006.01) |
| *A61K 38/08* | (2019.01) |
| *A61K 31/7088* | (2006.01) |
| *A61P 11/00* | (2006.01) |

(52) U.S. Cl.
CPC .............. *C07K 7/06* (2013.01); *A61K 31/166* (2013.01); *A61K 31/7088* (2013.01); *A61K 38/08* (2013.01); *A61K 45/06* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 9,067,968 | B2 | 6/2015 | Neville |
| 10,738,079 | B2 * | 8/2020 | Koval .............. A61K 31/7088 |
| 2004/0038370 | A1 | 2/2004 | Youakim |
| 2004/0077540 | A1 * | 4/2004 | Quay .................. A61K 9/0043 424/94.64 |
| 2005/0266421 | A1 | 12/2005 | Bird |

FOREIGN PATENT DOCUMENTS

WO 2002014499 2/2002

OTHER PUBLICATIONS

Baumgartner et al. A D-peptide analog of the second extracellular loop of claudin-3 and -4 leads to mis-localized claudin and cellular apoptosis in mammary epithelial cells, Chem Biol Drug Des. 2011, 77(2): 124-136.
Cornely et al. Two common human CLDN5 alleles encode different open reading frames but produce one protein isoform, Ann N Y Acad Sci. 2017, 397(1):119-129.
Fernandez et al. Chronic alcohol ingestion alters claudin expression in the alveolar epithelium of rats, Alcohol. 2007, 41(5): 371-379.
Neuhaus et al. Reversible opening of the blood-brain barrier by claudin-5-binding variants of Clostridium perfringens enterotoxin's claudin-binding domain, Biomaterials, 2018, 161, 129-143.
Schlingmann et al. Claudins: gatekeepers of lung epithelial function, Semin Cell Dev Biol. 2015, 42: 47-57.
Schlingmann et al. Regulation of claudin/zonula occludens-1 complexes by hetero-claudin interactions, Nat Commun. 2016, 7:12276.
Smith et al. Effects of different routes of endotoxin injury on barrier function in alcoholic lung syndrome, Alcohol, 2018.
Vyas-Read et al. Hyperoxia induces paracellular leak and alters claudin expression by neonatal alveolar epithelial cells, Pediatric Pulmonology. 2018, 53:17-27.
Wang et al. Heterogeneity of Claudin Expression by Alveolar Epithelial Cells, Am J Respir Cell Mol Biol. 2003, vol. 29, pp. 62-70.

\* cited by examiner

*Primary Examiner* — Maury A Audet
(74) *Attorney, Agent, or Firm* — Emory Patent Group

(57) ABSTRACT

This disclosure relates to compositions for use in managing respiratory distress and related disorders. In certain embodiments, the disclosure relates to methods of treating or preventing respiratory distress comprising administering an effective amount of a pharmaceutical composition comprising peptides or agents disclosed herein to a subject in need thereof. In certain embodiments, the peptides or agents decrease the concentration of claudin-5 in cells and tissues of the lungs.

18 Claims, 7 Drawing Sheets

Specification includes a Sequence Listing.

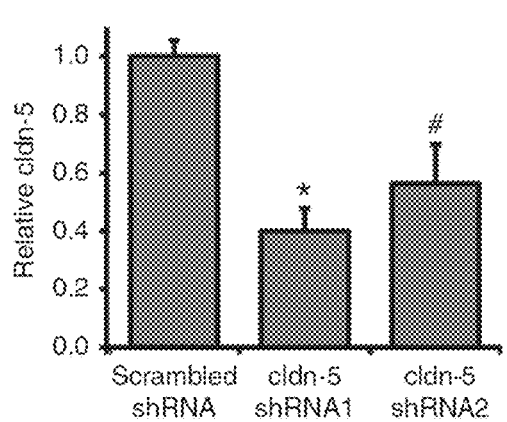
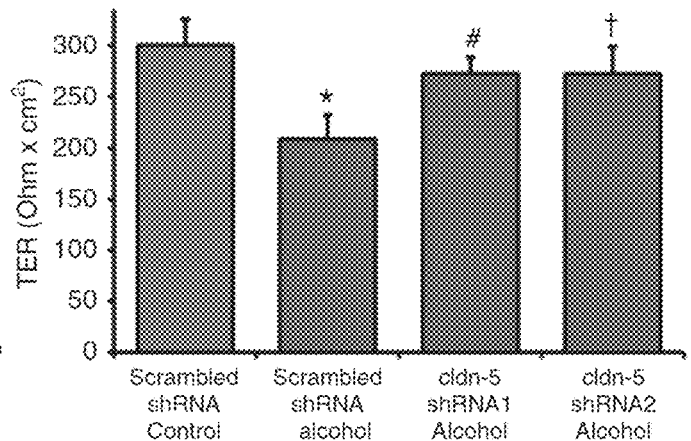
FIG. 1D
FIG. 1E
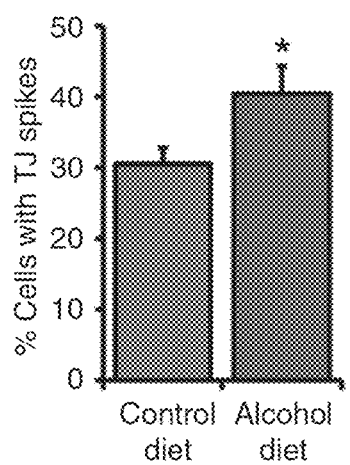
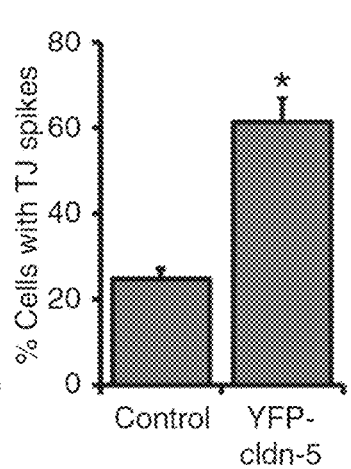
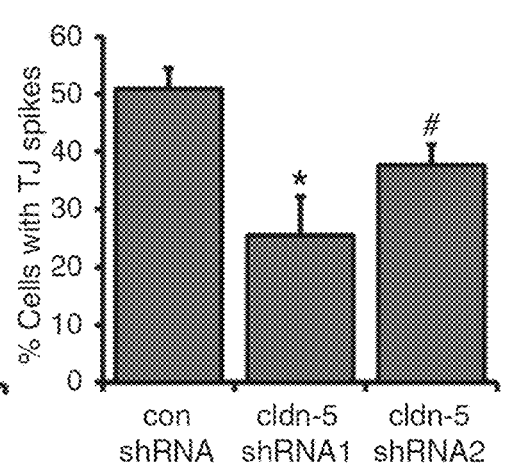
FIG. 2A
FIG. 2B
FIG. 2C

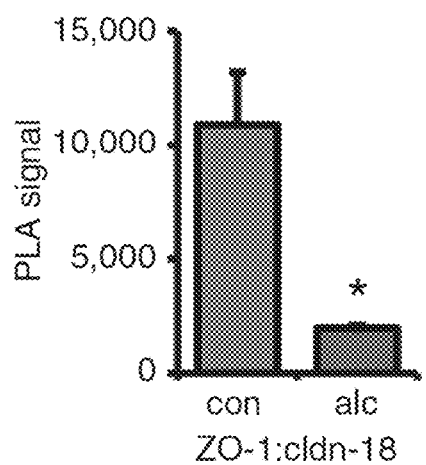
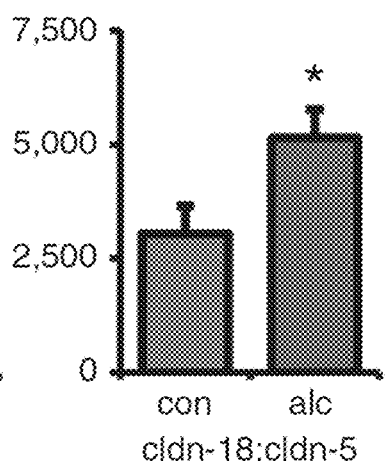
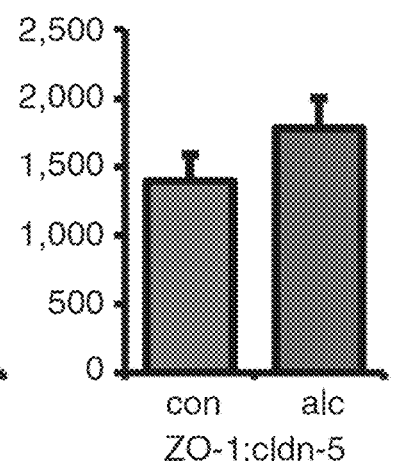
FIG. 5A    FIG. 5B    FIG. 5C
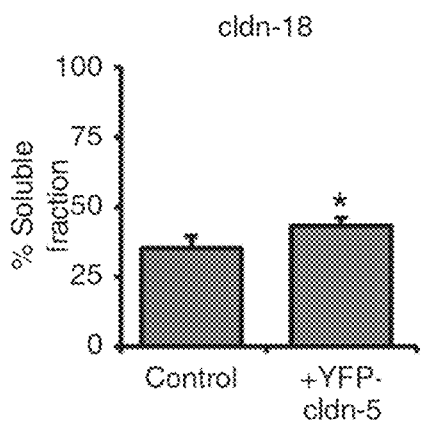
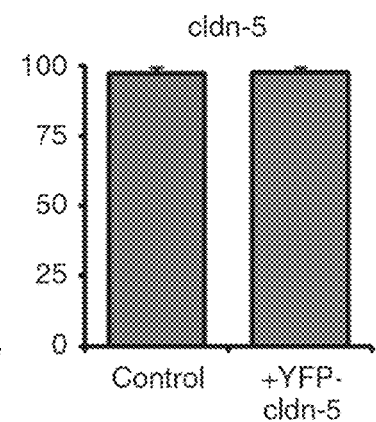
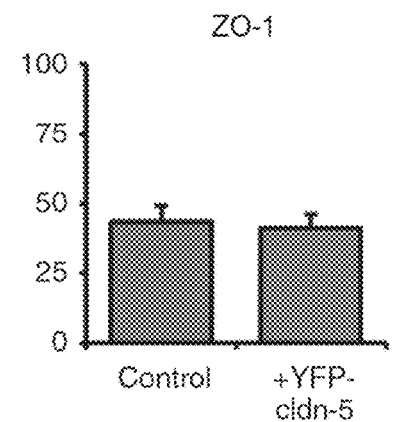
FIG. 6A    FIG. 6B    FIG. 6C

COMPOSITIONS AND METHODS FOR MANAGING RESPIRATORY CONDITIONS

CROSS-REFERENCE TO RELATED APPLICATIONS

This application is a division of U.S. application Ser. No. 15/953,133 filed Apr. 13, 2018, which claims the benefit of U.S. Provisional Application No. 62/485,552 filed Apr. 14, 2017. The entirety of each of these applications is hereby incorporated by reference for all purposes.

STATEMENT REGARDING FEDERALLY SPONSORED RESEARCH OR DEVELOPMENT

This invention was made with government support under HL116958 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 17072USDIV_ST25.txt. The text file is 8 KB, was created on Jun. 30, 2020, and is being submitted electronically via EFS-Web.

BACKGROUND

The lung is the essential respiratory organ. The principal function is to transport oxygen from the atmosphere into the bloodstream and to release carbon dioxide from the bloodstream into the atmosphere. In order for gas exchange to occur, the lung maintains a highly specialized barrier between the atmosphere and fluid-filled tissues. The terminal airspaces of the lung (alveoli), where gas exchange occurs, provide this barrier. The alveoli are covered by a layer of epithelial cells, alveoli epithelial cells (AECs). AECs act as barrier to fluid leakage and regulate ion transport to promote absorption from the alveolar space to enable proper gas exchange. Conversely, insults that compromise the alveolar epithelial barrier promote accumulation of fluid within the air space that severely compromises respiration.

Acute respiratory distress syndrome (ARDS) is characterized by a severe deficiency of oxygen in the bloodstream caused by alveolar inflammation resulting in the accumulation of fluid in the airspaces. ARDS is associated with mortality. Thus, there is a need to identify therapeutic strategies.

Wang et al. report heterogeneity of claudin expression by alveolar epithelial cells. Am. J. Respir. Cell. Mol. Biol. 29, 62-70 (2003).

Fernandez et al. report chronic alcohol ingestion alters claudin expression in the alveolar epithelium of rats. Alcohol 41, 371-379 (2007).

Baumgartner et al. report D-peptide analog of the second extracellular loop of claudin-3 and -4 leads to mislocalized claudin and cellular apoptosis in mammary epithelial cells. Chem. Biol. Drug Des. 77, 124-136 (2011).

References cited herein are not an admission of prior art.

SUMMARY

This disclosure relates to compositions for use in managing respiratory distress and related disorders. In certain embodiments, the disclosure relates to methods of treating or preventing respiratory distress comprising administering an effective amount of a pharmaceutical composition comprising peptides or agents disclosed herein to a subject in need thereof. In certain embodiments, the peptides or agents decrease the concentration of claudin-5 in cells and tissues of the lungs.

In certain embodiments, the peptides are claudin-5 mimetic peptides with an amino acid sequence corresponding to the region of the second extracellular (E2) domain adjacent to the third transmembrane (TM3) domain of claudin-5. In certain embodiments, this disclosure relates to a peptide having SEQ ID NO: 1 (EFYDP), derivatives, prodrugs, or salts thereof. In certain embodiments, proline (P) is a D-isomer, aspartic acid (D) is a D-isomer, tyrosine (Y) is a D-isomer, phenylalanine (F) is a D-isomer, glutamic acid (E) is a D-isomer, or combinations thereof. In certain embodiments, all of the amino acids are D-isomers.

In certain embodiments, the pharmaceutical agents are interfering RNA such short hairpin RNA (shRNA) that decrease claudin-5 expression by alveolar epithelial cells (AECs).

In certain embodiments, the disclosure contemplates the use of peptides or agents that prevent claudin-5 from causing claudin-18 and other barrier forming claudins to dissociate from ZO-1 and other proteins that promote claudins to form barriers. In certain embodiments, the disclosure contemplates the use of peptides or agents disclosed herein that prevent claudin-18 to dissociate from ZO-1. It is also contemplated that claudin-5 disrupts other claudins besides claudin-18.

In certain embodiments, this disclosure relates to methods of managing respiratory conditions or diseases using pharmaceutical agents that decrease in the number of alveolar epithelial cells (AECs) with tight-junction spikes using agents such as Dynasore (chemical name, N'-(3,4-dihydroxybenzylidene)-3-hydroxy-2-naphthohydrazide) or salts thereof.

In certain embodiments, the disclosure contemplates compositions comprising peptides or agents disclosed herein and a pharmaceutically acceptable excipient. In certain embodiments, the disclosure contemplates pharmaceutical composition comprising a peptide, or other pharmaceutical agent disclosed herein, or pharmaceutically acceptable salts thereof, and a pharmaceutically acceptable excipient. In certain embodiments, the pharmaceutical composition is in the form of a sterilized pH buffered aqueous salt solution or a saline phosphate buffer between a pH of 6 to 8, optionally comprising a saccharide or polysaccharide. In certain embodiments, the pharmaceutically acceptable excipient are aerosolizing agents, phospholipids or pulmonary surfactants. In certain embodiments, the aerosolizing agent is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the phospholipids are dipalmitoylphosphatidylcholine, palmitoyl-oleoyl phosphatidylglycerol, phosphatidylglycerol, or combinations thereof.

In certain embodiments, the disclosure contemplates methods of treating or preventing respiratory distress comprising administering an effective amount of a pharmaceutical composition comprising a peptide or agent disclosed herein to a subject in need thereof. In certain embodiments, the subject is diagnosed with alcoholic lung syndrome; acute respiratory distress syndrome; sepsis-associated lung disorders; bacterial and viral pneumonia; ventilator induced lung injury; bronchopulmonary dysplasia (BPD); asthma; bronchial, allergic, intrinsic, extrinsic or dust asthma; chronic or inveterate asthma; late asthma or airways hyper-responsiveness; chronic obstructive pulmonary disease (COPD); allergic rhinitis; bronchitis; emphysema; or cystic fibrosis. In certain embodiments, the peptide is administered in combination with another respiratory agent, anti-inflammatory agent, or antibiotic.

In certain embodiments, the disclosure contemplates recombinant nucleic acids vectors and cells comprising a nucleic acid that encodes peptides disclosed herein.

BRIEF DESCRIPTION OF THE DRAWINGS

FIG. 1D shows data indicating Claudin-5 was significantly depleted by specific shRNAs versus scrambled shRNA treated cells (n=4, *P=0.006, #P=0.036, one way ANOVA). Claudin-5 protein expression in alcohol-exposed AECs was depleted using a lentiviral system delivering shRNA targeting claudin-5 or control scrambled shRNAs.

FIG. 1E shows data indicating decreased claudin-5 expression in alcohol-exposed cells significantly increased TER as compared with cells transduced with scrambled shRNAs (n=4, #P<0.001, †P<0.001, one way ANOVA). TER of cells from alcohol exposed cells treated with shRNA was significantly lower than comparable control cells (n=4, *P<0.001, one way ANOVA).

FIG. 2A shows control versus alcohol data on the quantification of the % of cells containing 3 or more tight junction spikes oriented towards the nucleus demonstrated that alcohol exposed and YFP-claudin-5 transduced AECs had significantly more spikes than comparable controls (*P=0.035, unpaired two-tailed t-test, n=11 fields).

FIG. 2B shows data on EGFP versus YFP-claudin-5 (*P<0.001, unpaired two-tailed t-test, n=11 fields).

FIG. 2C shows data indicating alcohol exposed AECs transduced with claudin-5 shRNA1 had significantly fewer spikes than cells treated with control shRNA (*P=0.011, one way ANOVA with Tukey multiple comparisons test, n=5 fields). Cells treated with shRNA2 showed a trend towards decreased spikes (#P=0.18, one way ANOVA with Tukey multiple comparisons test, n=5).

FIG. 5A shows data on the quantification of co-localization using PLA demonstrated a significant change. In alcohol-exposed AECs there was a significant decrease in ZO-1: claudin-18 (n=6 fields, *P=0.018, unpaired two-tailed t-test).

FIG. 5B shows data indicating a correlation with a significant increase in claudin-18:claudin-5 co-localization (n=10 fields, *P=0.026, unpaired two-tailed t-test)

FIG. 5C show data indicating ZO-1:claudin-5 co-localization was unchanged (n=6 fields, unpaired two-tailed t-test).

FIG. 6A shows data of biochemical analysis of protein insolubility was assessed by a Triton X-100 solubilization assay comparing control AECs to YFP-claudin-5 transduced cells. At 6 days in culture, AECs were harvested and extracted using 0.1% Triton X-100, an aliquot of total protein (T) was set aside and the remainder was centrifuged to separate Triton X-100 soluble (S) and insoluble (I) fractions that were measured by immunoblot for claudin-18. Quantification of the soluble fraction revealed that YFP-claudin-5 expression significantly increased claudin-18 solubility from 35.2%±1.8 to 42.1%±0.6 while claudin-5 and ZO-1 solubility did not significantly change (n=3, *P=0.003, unpaired two-tailed t-test).

FIG. 6B shows data for claudin-5 (n=3, *P=0.003, unpaired two-tailed t-test).

FIG. 6C shows data for ZO-1(n=3, *P=0.003, unpaired two-tailed t-test).

DETAILED DISCUSSION

Figure 1A:
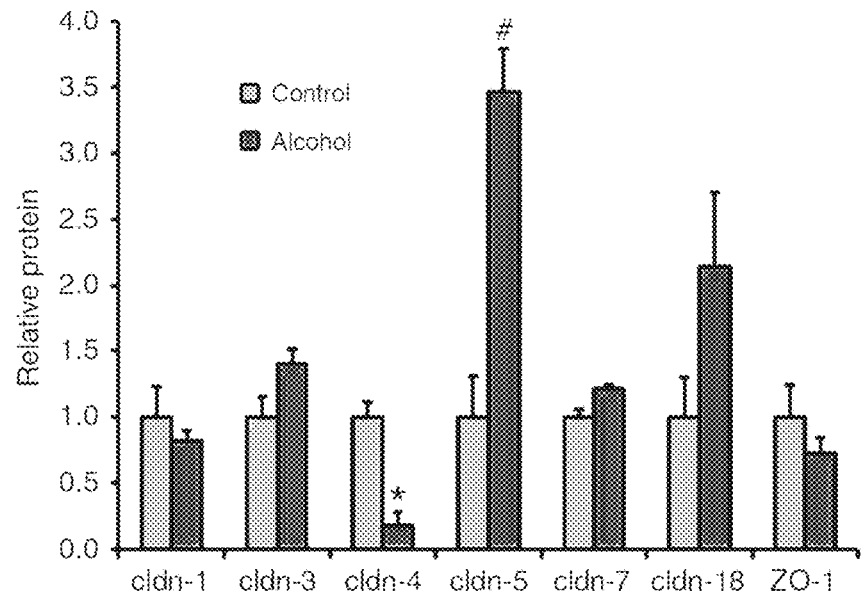
FIG. 1A shows immunoblot data indicating alcohol exposure significantly decreased claudin-4 expression (n=3, *P=0.002, t-test) and significantly increased claudin-5 expression (n=3, #P=0.005, t-test) by alveolar epithelial cells (AECs).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

"Subject" refers any animal, preferably a human patient, livestock, or domestic pet.

The terms "protein" and "peptide" refer to compounds comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

As used herein, the term "derivative" refers to a structurally similar peptide that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more peptides linked together by a linking group. It is contemplated that the linking group may be biodegradable. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent.

When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, $2^{nd}$. Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

The term "prodrug" refers to an agent that is converted into a biologically active form in vivo. Prodrugs are often useful because, in some situations, they may be easier to administer than the parent compound. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein an hydroxy, amino or mercapto (thiol) group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed peptide or a pharmaceutically acceptable form of the peptide contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_2$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

If a disclosed peptide or a pharmaceutically acceptable form of the peptide contains an alcohol functional group, a prodrug can be formed by the replacement of the hydrogen atom of the alcohol group with a group such as ($C_1$-$C_6$) alkanoyloxymethyl, 1-(($C_1$-$C_6$)alkanoyloxy) ethyl, 1-methyl-1(($C_1$-$C_6$)alkanoyloxy)ethyl ($C_1$-$C_6$)alkoxycarbonyloxymethyl, —N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from amino acids P(O)(OH)$_2$, —P(O)(O($C_1$-$C_6$)alkyl)$_2$, and glycosyl (the radical resulting from the removal of a hydroxyl group of the hemiacetal form of a carbohydrate).

If a disclosed peptide or a pharmaceutically acceptable form of the peptide incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural alpha-aminoacyl, —C(OH)C(O)OY$_1$ wherein $Y^1$ is H, ($C_1$-$C_6$)alkyl or benzyl, —C(OY$_2$)Y$_3$ wherein Y$_2$ is ($C_1$-$C_4$) alkyl and Y$_3$ is ($C_1$-$C_6$)alkyl, carboxy($C_1$-$C_6$)alkyl, amino($C_1$-$C_4$)alkyl or mono-Nor di-N,N-($C_1$-$C_6$)alkylaminoalkyl, —C(Y$_4$)Y$_5$ wherein Y$_4$ is H or methyl and Y$_5$ is mono-N- or di-N,N-($C_1$-$C_6$)alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

A "linking group" refers to any variety of molecular arrangements that can be used to bridge to molecular moieties together. An example formula may be —R$_m$— wherein R is selected individually and independently at each occurrence as: —CR$_m$R$_m$—, —CHR$_m$—, —CH—, —C—, —CH$_2$—, —C(OH)R$_m$, —C(OH)(OH)—, —C(OH)H, —C(Hal)R$_m$—, —C(Hal)(Hal)—, —C(Hal)H—, —C(N$_3$) R$_m$—, —C(CN)R$_m$—, —C(CN)(CN)—, —C(CN)H—, —C(N$_3$)(N$_3$)—, —C(N$_3$)H—, —O—, —S—, —NH—, —NR$_m$—, —(C=O)—, —(C=NH)—, —(C=S)—, —(C=CH$_2$)—, which may contain single, double, or triple bonds individually and independently between the R groups. If an R is branched with an R$_m$ it may be terminated with a group such as —CH$_3$, —H, —CH=CH$_2$, —CCH, —OH, —SH, —NH$_2$, —N$_3$, —CN, or -Hal, or two branched Rs may form a cyclic structure. It is contemplated that in certain instances, the total Rs or "m" may be less than 100, or 50, or 25, or 10. Examples of linking groups include bridging alkyl groups and alkoxyalkyl groups. Linking groups may be substituted with one or more sub stituents.

As used herein, the term "biodegradable" in reference to a substituent or linker refers to a molecular arrangement in a peptide derivative that when administered to a subject, e.g., human, will be broken down by biological mechanism such that a metabolite will be formed and the molecular arrangement will not persist for over a long period of time, e.g., the molecular arrangement will be broken down by the body after a several hours or days. In certain embodiments, the disclosure contemplates that the biodegradable linker or substituent will not exist after a week or a month.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "sterilized" refers to subjecting something to a process that effectively kills or eliminates transmissible agents (such as fungi, bacteria, viruses, prions and spore forms etc.). Sterilization can be achieved through application of heat, chemicals, irradiation, high pressure or filtration. One process involves water prepared by distillation and stored in an airtight container wherein suitable additives are introduced to approximate isotonicity.

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements.

A "heterologous" nucleic acid sequence or peptide sequence refers to a nucleic acid sequence or peptide sequence that do not naturally occur, e.g., because the whole sequences contain a segment from other plants, bacteria, viruses, other organisms, or joinder of two sequences that occur the same organism but are joined together in a manner that does not naturally occur in the same organism or any natural state.

Regulation of Claudin/Zonula Occludens-1 Complexes by Hetero-Claudin Interactions Although there are a number of diseases and conditions that can lead to acute respiratory distress syndrome (ARDS), studies identified alcohol abuse emerged as the only independent risk factor known to increase the odds of any given at-risk individual developing ARDS. Chronic alcohol consumption is associated with diminished lung barrier function in patients.

Tight junctions in the lungs are composed of several different classes of transmembrane, cytosolic and cytoskeletal proteins which interact in a coordinated manner to form epithelial barriers at cell to cell contact regions. Claudins, a family of tetraspan transmembrane proteins with 27 members, form the structural basis for control of tight junction permeability. They associate with other claudins in adjacent cells and seal the gaps between them to create a regulated barrier to paracellular diffusion across the epithelia. Interactions between claudins are important for barrier function. In order to form a functional barrier, claudins interact with each other within the same cellular membrane (polymeric cis-interactions) and between two cells via head-to-head interactions (polytypic trans-interactions). Claudin interactions can be classified as homomeric (polymeric cis-interaction) and homotypic (trans-interaction) when the polymer consists of the same claudin.

Over a dozen different claudins have been found in the alveolar epithelium including claudin-1, -3, -4, -5, -7 and -18. Claudin structure plays an important role in tight junction formation. Claudins have four transmembrane domains, two extracellular loops, one intracellular loop as well as a cytoplasmic localized N- and C-terminus.

Dietary alcohol significantly impairs alveolar epithelial cell (AEC) tight junctions that are required to provide a barrier between fluid-filled tissues and the airspace. However, the molecular basis for the effects of alcohol on alveolar epithelial tight junctions is not well understood. Isolated primary rat AECs that differentiate into a model type-I monolayer were studied at a molecular level. Rats fed dietary alcohol for 8 weeks provide an animal model system that recapitulates the pathologic consequences of chronic alcohol ingestion on lung barrier function. Moreover, primary cells derived from alcohol-fed rats (alcohol-exposed AECs) have impaired barrier function that persists in vitro, as compared with AECs isolated from animals fed an isocaloric control diet.

AECs from alcohol-fed animals have significant changes in tight-junction protein expression that are associated with a decrease in epithelial barrier function. Among these changes is an increase in claudin-5 expression. By molecular manipulation of AECs, it was discovered that claudin-5 is both necessary and sufficient to disrupt AEC tight junctions. Increased claudin-5 expression induces the formation of claudin-containing structures perpendicular to the axis of the cell-cell interface (tight-junction spikes) that are active sites of vesicle budding and fusion. The appearance of tight-junction spikes correlates with increased paracellular leak between AECs. Using several complementary approaches, it was discovered that claudin-5 interacted with claudin-18, and that this decreases the ability of claudin-18 to productively interact with zonula occludens 1 (ZO-1). This mechanism is targetable using a claudin-5 mimetic peptide, indicating a potential therapeutic approach to promote alveolar barrier function.

Increased claudin-18:claudin-5 interactions decreased ZO-1:claudin-18 co-localization, which correlated with weakened assembly into tight junctions as evidenced by an increase in Triton X-100 solubility. The net effect of decreased interactions between claudin-18 and ZO-1 is to destabilize tight junctions that, in turn, increases paracellular leak.

Two examples of claudin-claudin interactions that occur before delivery to the plasma membrane are claudin-4: claudin-8, and claudin-16:claudin-19. In each of those cases, depletion or misfolding of one claudin resulted in intracellular accumulation of the other, evidence that these pairs of claudins serve as co-chaperones. Interestingly, in kidney epithelia, claudin-18 trafficking was independent of claudin-16 and claudin-19, indicating specificity of cis-claudin interactions. In AECs, the intracellular pools of claudin-5 and claudin-18 are limited, largely vesicular and do not show complete co-localization. As the effects of claudin-5 on claudin-18 largely affect tight-junction morphology in AECs, and that these effects are antagonized by a claudin-5 extracellular mimetic peptide, it seems more likely to be that claudin-5 and claudin-18 interact within tight junctions or other regions of the plasma membrane rather than before delivery. Considering that tight-junction-associated claudins are highly dynamic there is certainly the capacity for claudin remodelling to occur within pre-formed tight junctions at cell-cell interfaces as well as in claudins newly delivered to the plasma membrane.

Cis interactions between claudin-5 and claudin-18 can diminish barrier function by affecting the ability of claudin-18 to form complexes with ZO-1. Cis interactions between claudin-5 and claudin-3 have previously been characterized at a molecular level. It was unknown that claudin-5 can regulate the ability of claudin-18, to interact with the cytoplasmic scaffold including claudin-5 interfering with other lung claudins.

Claudin-5 increased formation of tight-junction spikes that, in turn, correlated with increased paracellular leak. Association of tight-junction spikes with increased paracellular permeability is consistent with reports demonstrating that spikes and barrier dysfunction are also induced by transforming growth factor-β1 and nuclear factor-κB inhibitors. Normal AECs treated with the nuclear factor-κB inhibitor BMS-345541 showed both increased claudin-5 expression and increased formation of tight-junction spikes as a result of interfering with granulocyte-macrophage colony-stimulating factor signaling that mimics the effects of alcohol on AECs. Here, live-cell imaging was used to confirm that these were sites where claudin-containing vesicles were observed to bud and fuse from the ends of spikes. Linking tight-junction spikes and enhanced endocytosis with a decrease in barrier function is also consistent with treatment of fetal AECs with endocytosis inhibitors almost doubled transepithelial resistance (TER).

Given that tight-junction spikes are associated with alcohol and claudin-5 expression, and that these are sites of active vesicle trafficking of claudin-containing vesicles, increased claudin-5 accounts for the deleterious effects of dietary alcohol on AEC barrier function. The effects of increased claudin-5 appear to contradict the role of claudin-5 in promoting endothelial barrier function. Data herein indicates that claudin-5 function is cell type dependent and is influenced by the context of expression. For example, claudin-5 has the capacity to increase barrier function of MDCK II cells, which are otherwise exceptionally leaky, with baseline TER in the range of 100Ω×cm2. In AECs, which are much tighter, claudin-5 had the opposite effect. It is also possible that the ability of claudin-5 to impair tight junctions is specifically dependent on an interaction with claudin-18, which is not present in MDCK cells. A specific interaction between claudin-5 and claudin-18 has particular relevance to alveolar barrier function. Although it is not intended that embodiments of this disclosure be limited by any particular mechanism, the mechanism by which alcohol induces claudin-5 expression is under investigation at present and could either be transcriptional or posttranslational.

As claudin-5 has a dramatic effect on AEC barrier function, it represents an appealing potential pharmacologic target to improve alveolar barrier function in vulnerable individuals, using a claudin-5 mimetic peptide (Ac-EFYDP (SEQ ID NO: 1)-NH$_2$). The feasibility of this approach was confirmed. The peptide specifically increased barrier function of alcohol-exposed AECs. The D-amino acid version of an Ac-DFYNP-NH$_2$ mimetic is 10-100-fold more effective than the corresponding L-amino acid version. Unlike the DFYNP sequence that is shared by several claudins important for lung barrier function, including claudin-3 and claudin-4, the EFYDP (SEQ ID NO: 1) corresponding to claudin-5 is unlikely to cross-react with other non-homologous claudins and claudin-1 expression in the lung is low and unaffected by the peptide.

EFYDP (SEQ ID NO: 1) is in the E2 region of the protein directly adjacent to the TM3 domain, a region of claudin-5 that mediates cis-claudin interactions which is consistent with the idea that claudin-5 interactions with claudin-18 have a deleterious effect on the ability of claudin-18 to interact with ZO-1. The ability of a cis-claudin interaction to affect interactions of another claudin with the tight-junction scaffold represents a novel mode of tight-junction regulation with the potential to be pharmacologically manipulable. Specific and direct targeting of claudin-5 using these approaches offers the potential of preventing acute respiratory distress syndrome, particularly in those individuals at greatest risk due to underlying alcohol abuse, by improving alveolar barrier function and fluid clearance.

Peptide Mimetics, Derivatives, and Prodrugs

In certain embodiments, the pharmaceutical agents are claudin-5 mimetic peptides corresponding to the region of the second extracellular (E2) domain adjacent to the third transmembrane (TM3) domain of claudin-5. In certain embodiments, this disclosure relates to methods of pharmaceutical management using pharmaceutical agents such as a peptide having SEQ ID NO: 1 (EFYDP), derivatives, prodrugs, or salts thereof. In certain embodiments, proline (P) is a D-isomer, aspartic acid (D) is a D-isomer, tyrosine (Y) is a D-isomer, phenylalanine (F) is a D-isomer, glutamic acid (E) is a D-isomer, or combinations thereof. In certain embodiments, all of the amino acids are D-isomers.

In certain embodiments, a peptide derivative is one where glutamic acid (E) comprises an N-terminal alkanoyl group optionally substituted with one or more substituents. In certain embodiments, a peptide derivative is one where glutamic acid (E) comprises an alkyl carboxy ester group optionally substituted with one or more substituents. In certain embodiments, a peptide derivative is one where phenylalanine (F) comprises a phenyl group optionally substituted with one or more substituents. In certain embodiments, a peptide derivative is one where aspartic acid (D) comprises an alkyl carboxy ester group optionally substituted with one or more substituents. In certain embodiments, a peptide derivative is one where proline (P) comprises a C-terminal amide optionally substituted with one or more substituents.

In certain embodiments, the disclosure contemplates peptides disclosed herein having at least one molecular modification, e.g., such that the peptide contains a non-naturally amino acid. In certain embodiments, the disclosure contemplates a non-naturally occurring derivative of a peptide having SEQ ID NO: 1. In certain embodiments, the disclosure contemplates a derivative in the form of a prodrug. In certain embodiments, the disclosure contemplates a derivative wherein an amino, carboxyl, or hydroxyl group in a peptide disclosed herein is substituted. In certain embodiments, the disclosure contemplates peptides disclosed herein having a label, e.g., fluorescent or radioactive. In certain embodiments, the peptide comprises a non-naturally occurring amino acid. In certain embodiments, the peptide comprises an amino acid comprising a halogen.

In certain embodiments, the disclosure contemplates derivatives of SEQ ID NO: 1 (EFYDP) that are amino acid substitutions wherein amino acid E can be D; F can be Y or W; and Y can be F or W.

In certain embodiments, a peptide of this disclosure has the following formula

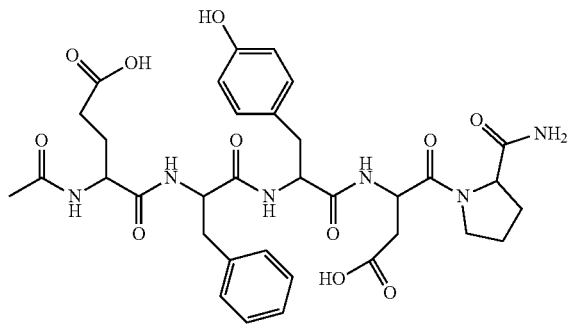 [SMILES: CC(=O)NC(CCC(=O)O)C(=O)NC(Cc1ccccc1)C(=O)NC(Cc1ccc(O)cc1)C(=O)NC(CC(=O)O)C(=O)N1CCCC1C(N)=O]

derivatives, prodrugs, esters, or salts thereof.

The peptides of this disclosure may be made from using commercially available BOC and Fmoc protected amino acids using well-known synthetic procedures for amide coupling, e.g., using solid phase resins. Acid halides of amide coupling reactions can be used to N-terminally modify the peptide. Carboxylic acids may be exposed to alcohols in the presence of an acid to form esters. Carboxylic acids may be converted to activated intermediates that react with ammonia or other substituted amines to form C-terminal amides or amides of glutamic or aspartic acid. Alternatively, the peptides can be prepared by expression systems that utilize recombinant nucleic acids encoding the peptides or fusion peptides. The fusion peptides may be exposed to cleaving agents or the fusion peptides may contain self-cleaving sequences allowing the peptide product to be isolated and optionally further modified.

In certain embodiments, the peptides discloses herein have at least one non-naturally occurring molecular modification, such as the attachment of polyethylene glycol, the attachment of a chimeric peptide, the attachment of a fluorescent dye comprising aromatic groups, fluorescent peptide, a chelating agent capable of binding a radionuclide such as $^{18}$F, N-terminal acetyl, propionyl group, myristoyl and palmitoyl, group or N-terminal methylation, or a C-terminal alkyl ester. In certain embodiments, the disclosure contemplates the disclosure contemplates peptides disclosed herein labeled using commercially available biotinylation reagents. Biotinylated peptide can be used in streptavidin affinity binding, purification, and detection.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amino acid containing a carboxylic acid side chain group such as aspartic acid or glutamic acid, within the peptide comprising a sequence disclosed herein.

In certain embodiments, the disclosure relates to recombinant polypeptides comprising sequences disclosed herein or fusions thereof wherein the amino terminal end or the carbon terminal end of the amino acid sequence are optionally attached to a heterologous amino acid sequence, label, or reporter molecule.

Thus, in certain embodiments, the disclosure contemplates recombinant nucleic acids vectors and cells comprising the same. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein. In certain embodiments, the disclosure relates to a vector comprising the nucleic acid encoding a peptide disclosed herein and a heterologous nucleic acid sequence.

The terms "vector" or " expression vector " refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Proteins may be recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA co-factors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme that confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to the recombinant vectors comprising a nucleic acid encoding a polypeptide disclosed herein or fusion protein thereof. In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, the disclosure relates to a nucleic acid encoding a polypeptide disclosed herein wherein the nucleotide sequence has been changed to contain at least one non-naturally occurring substitution and/or modification relative to the naturally occurring sequence, e.g., one or more nucleotides have been changed relative to the natural sequence. In certain embodiments, the disclosure relates to a nucleic acid encoding a polypeptide disclosed herein further comprising a label.

Interfering Claudin-5 MRNA Nucleobase Polymers

In certain embodiments, the disclosure contemplates inhibition of claudin-5 mRNA, e.g., the use of nucleobase polymers for antisense disruptions or RNA interference of Claudin-5 mRNA expression or Claudin-5 mRNA binding in order to decrease Claudin-5 mRNA expression as a therapeutic strategy.

In certain embodiments, the disclosure contemplates methods of treating or preventing respiratory distress comprising administering an effective amount of a pharmaceutical composition comprising a nucleobase polymers for antisense disruptions or RNA interference of Claudin-5 mRNA expression disclosed herein to a subject in need thereof. In certain embodiments, the subject is diagnosed with alcoholic lung syndrome; acute respiratory distress syndrome; sepsis-associated lung disorders; bacterial and viral pneumonia; ventilator induced lung injury; bronchopulmonary dysplasia (BPD); asthma; bronchial, allergic, intrinsic, extrinsic or dust asthma; chronic or inveterate asthma; late asthma or airways hyper-responsiveness; chronic obstructive pulmonary disease (COPD); allergic rhinitis bronchitis, emphysema; or cystic fibrosis. In certain embodiments, the peptide is administered in combination with another respiratory agent, anti-inflammatory agent, or antibiotic.

There are two human Claudin-5 mRNAs with NCBI accession numbers NM_001130861.1 and NM_003277.3. See Comely et al. Two common human CLDN5 alleles encode different open reading frames but produce on protein isoform. In NM_001130861, bases 1083-1739 which encode claudin-5 are (SEQ ID NO: 2)

```
ATGGGGTCCGCAGCGTTGGAGATCCTGGGCCTGGTGCTGTGCCTGGTGG

GCTGGGGGGTCTGATCCTGGCGTGCGGGCTGCCCATGTGGCAGGTGAC

CGCCTTCCTGGACCACAACATCGTGACGGCGCAGACCACCTGGAAGGGG

CTGTGGATGTCGTGCGTGGTGCAGAGCACCGGGCACATGCAGTGCAAAG

TGTACGACTCGGTGCTGGCTCTGAGCACCGAGGTGCAGGCGGCGCGGGC

GCTCACCGTGAGCGCCGTGCTGCTGGCGTTCGTTGCGCTCTTCGTGACC

CTGGCGGGCGCGCAGTGCACCACCTGCGTGGCCCCGGGCCCGGCCAAGG

CGCGTGTGGCCCTCACGGGAGGCGTGCTCTACCTGTTTTGCGGGCTGCT

GGCGCTCGTGCCACTCTGCTGGTTCGCCAACATTGTCGTCCGCGAGTTT

TACGACCCGTCTGTGCCCGTGTCGCAGAAGTACGAGCTGGGCGCAGCGC

TGTACATCGGCTGGGCGGCCACCGCGCTGCTCATGGTAGGCGGCTGCCT

CTTGTGCTGCGGCGCCTGGGTCTGCACCGGCCGTCCCGACCTCAGCTTC

CCCGTGAAGTACTCAGCGCCGCGGCGGCCCACGGCCACCGGCGACTACG

ACAAGAAGAACTACGTCTGA.
```

In certain embodiments, the nucleobase polymer has a sequence of more than 7, 8, 9, 10, 11, 12, 13, 14, 15 or more nucleotides or nucleobases or continuous nucleotide nucleobases that is the reverse complement of the protein encoding region of NM_001130861.1 or NM_003277.3, the non-coding regions of NM_001130861.1 or NM_003277.3, SEQ ID NO: 2, or allelic variants thereof. In certain embodiments, the nucleobase polymer is less than 100, 50, or 25 nucleobases or base pairs. In certain embodiments, the nucleobase polymer is more than three nucleotides but less than seven or eight, or more than four nucleotides but less than seven or eight, or more than five nucleotides but less than seven or eight.

In certain embodiments, the nucleobase polymer comprises monomers of (LNA) 1-(hydroxymethyl)-2,5-dioxabicyclo[2.2.1]heptan-7-ol, ribose, deoxyribose, 2'-O-methy ribose, 2'-O-methoxyethyl ribose, 2'-fluororibose, phosphodiester, phosphorothioate, methylphosphonate, phosphorodiamidate, piperazine phosphorodiamidate, P-(2-(hydroxymethyl)morpholino)-N,N-dimethylphosphonamidate, morpholin-2-ylmethanol, (2-(hydroxymethyl)morpholino)(piperazin-1-yl)phosphinate, or peptide nucleic acids or combinations thereof.

In certain embodiments, pharmaceutical composition comprising a pharmaceutically acceptable excipient and a nucleobase polymer disclosed herein. In certain embodiments, the nucleobase polymer comprises SEQ ID NO: 2 or fragment or reverse complement thereof. In certain embodiments, the nucleobase polymer is double or single stranded. In certain embodiments, the fragment is greater than 5, 10, 15, or 20 nucleotides or nucleobases. In certain embodiments, the fragment is less than 100, 50, or 25 nucleotides or nucleobases or base pairs.

In certain embodiments, the disclosure relates to synthetic, non-naturally occurring nucleobase polymer comprising a sequence described herein or variants thereof. In certain embodiments, the variant has 98%, 95%, 90%, 85%, 80%, 75%, 70%, 65%, 60%, or 50% sequence identity thereto.

In certain embodiments, the disclosure relates to compositions, e.g., pharmaceutical compositions, and uses reported herein comprising short hairpin, synthetic, non-naturally occurring nucleobase polymer comprising TAGTTCTTCT (SEQ ID NO: 3), CGGTGGC(SEQ ID NO: 4), GGCGCTGA(SEQ ID NO: 5), GGAAGC(SEQ ID NO: 6), GACGGCCG(SEQ ID NO: 7), GCAGACC(SEQ ID NO: 8), ACAAGAGGCA(SEQ ID NO: 9), CCGCCCAGC(SEQ ID NO: 10), CGCTGCG(SEQ ID NO: 11), ACACGGGCACA(SEQ ID NO: 12), ACGACAATG(SEQ ID NO: 13), AGCAGCCCGC(SEQ ID NO: 14), GAGGGCCACACG (SEQ ID NO: 15), CGCCTTGGC(SEQ ID NO: 16), TGCACTGCGCG(SEQ ID NO: 17), AGGGTCACG(SEQ ID NO: 18), CACGGCG (SEQ ID NO: 19), GCCTGCACCTC(SEQ ID NO: 20), GAGTCGTACAC (SEQ ID NO: 21), ATGTGCCCGGT(SEQ ID NO: 22), CACAGCCCCTTCCA(SEQ ID NO: 23), GCGCCGTCACGA(SEQ ID NO: 24), TGCCACAT(SEQ ID NO: 25), ACGCCAGGATC(SEQ ID NO: 26), or combinations thereof optionally with monomers of 1-(hydroxymethyl)-2,5-dioxabicyclo[2.2.1]heptan-7-ol and/or one or more phosphorothioate linkages.

In certain embodiments, the disclosure relates to a vector having a nucleic acid encoding a hairpin comprising SEQ ID NO: 3-26. In certain embodiments, the disclosure contemplates methods of treating or preventing respiratory distress comprising administering an effective amount of pharmaceutical agent comprising a vector having a nucleic acid encoding a hairpin RNA comprising SEQ ID NO: 3-26 to a subject in need thereof. In certain embodiments, the subject is diagnosed with alcoholic lung syndrome; acute respiratory distress syndrome; sepsis-associated lung disorders; bacterial and viral pneumonia; ventilator induced lung injury; bronchopulmonary dysplasia (BPD); asthma; bronchial, allergic, intrinsic, extrinsic or dust asthma; chronic or inveterate asthma; late asthma or airways hyper-responsiveness; chronic obstructive pulmonary disease (COPD); allergic rhinitis, bronchitis, or cystic fibrosis. In certain embodiments, the peptide is administered in combination with another respiratory agent, anti-inflammatory agent, or antibiotic.

Pharmaceutical Compositions

In certain embodiments, the disclosure contemplates pharmaceutical composition comprising a peptide, or other pharmaceutical agent disclosed herein, or pharmaceutically acceptable salts thereof, and a pharmaceutically acceptable excipient. In certain embodiments, the pharmaceutical composition is in the form of a sterilized pH buffered aqueous salt solution. In certain embodiments, the pharmaceutically acceptable excipient is aerosolizing agent or phospholipids. In certain embodiments, the aerosolizing agent is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the phospholipid is dipalmitoylphosphatidylcholine, palmitoyl-oleoyl phosphatidylglycerol, phosphatidylglycerol, or combinations thereof.

In certain embodiments, the pharmaceutical compositions may be stored in a nebulizer, inhaler, or other container optionally sealed or under a pressure for propelling the pharmaceutical agent(s). The container may contain a spraying apparatus that is manually-actuated or pressurized. Metered dose inhalers (MDIs) typically have a handheld aerosol canister that, upon being pushed, releases an amount of medicine to inhale. Dry powder inhalers (DPIs) do not use a propellant to release the medicine. Instead, a dry powder form of the peptide or agent is drawn into your lungs after a breath. In certain configurations, a container comprising the peptide or agent is inserted a device. Pressing a button or section on the device pierces the container. One can breathe in the powder contained in the container through a mouthpiece on the device.

In certain embodiments, the pharmaceutical compositions may contain naturally or non-naturally occurring pulmonary surfactant compositions. Contemplated natural pulmonary surfactant compositions typically comprise 70-90% phospholipids (PC) such as dipalmitoylphosphatidylcholine (DPPC), phosphatidylcholine, and phosphatidylglycerol (PG); and 1-10% surfactant-associated proteins, apolipoproteins SP-A (SFTPA1), B (SFTPB), C (SFTPC) and D (SFTPD) (SP standing for "surfactant-associated protein"); and 1-10% Cholesterol (neutral lipids). Artificial pulmonary surfactants include colfosceril palmitate (Exosurf), a mixture of DPPC with hexadecanol and tyloxapol added as spreading agents; pumactant (Artificial Lung Expanding Compound or ALEC), a mixture of DPPC and PG; KL-4, composed of DPPC, palmitoyl-oleoyl phosphatidylglycerol, and palmitic acid, combined with a 21 amino acid synthetic peptide that mimics the structural characteristics of SP-B; and venticute, composed of DPPC, PG, palmitic acid and recombinant SP-C shares a nearly identical sequence with human SP-C except that the palmitoylated cysteines are absent and have been replaced with phenylalanines to eliminate protein oligomerization. Contemplated animal derived surfactants include beractant (Alveofact), extracted from cow lung lavage fluid and (Survanta), extracted from minced cow lung with additional DPPC, palmitic acid and tripalmitin; calfactant (Infasurf), extracted from calf lung lavage fluid; and poractant alfa (Curosurf)—extracted from material derived from minced pig lung.

In certain embodiments, the pharmaceutical compositions disclosed herein further comprise a respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate; a p38 antagonist such as losmapimod; a phosphodiesterase (PDE) inhibitor such as a methylxanthanine, theophylline, and aminophylline; a selective PDE isoenzyme inhibitor, a PDE4 inhibitor and the isoform PDE4D, such as tetomilast, roflumilast, oglemilast, ibudilast, ronomilast; a modulator of chemokine receptor function such as vicriviroc, maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as setileuton, licofelone, quiflapon, zileuton, zafirlukast, or montelukast; and a myeloperoxidase antagonist such as resveratrol and piceatannol.

Effective doses may be extrapolated from dose-response curves derived from in vitro or animal model test systems. For peptides or other agents, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of peptides or agent may be reduced by enhancing uptake and tissue penetration of the peptides or agents by modifications such as, for example, lipidation and the inclusion of natural or artificial pulmonary surfactants.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydroxypropyl(cyclodextrin), or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanuium dioxide, talc, corn starch, carnuba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, the pharmaceutical compositions is in solid form surrounded by an enteric coating, i.e., a polymer barrier applied on oral medication that prevents its dissolution or disintegration in the gastric environment. Compounds typically found in enteric coatings include methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, and combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be both natural and artificial pulmonary surfactants, sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with peptides or agents disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising peptides and agents disclosed herein and pharmaceutically acceptable excipient. In certain embodiments, this disclosure contemplates the production of a medicament comprising peptides or agents disclosed herein and uses for methods disclosed herein.

In certain embodiments, the disclosure relates to pharmaceutical compositions comprising peptides and agents disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo), preparations incorporated into pulmonary surfactants (both natural and artificial), and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the peptides or agents may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the peptides and agents, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, peptides and agents disclosed herein and a pharmaceutical carrier, are provided already in a combined dry form ready to be reconstituted together. In other embodiments, it is contemplated that peptides and agents disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated peptides or agents can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as inhalers, syringes, vials, tubes, etc. The pharmaceutical composition may then be applied via actuation or specific needles of the syringe or via suitable catheters. A typical diluent comprises water for injection, and NaCl (preferably 50 to 150 mM, especially 110 mM), $CaCl_2$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, this disclosure contemplates a kit comprising a pharmaceutical composition disclosed herein such as a peptide or agent and a container optionally with a suitable diluent. Further components of the kit may be instructions for use, administration means, such as inhalers, syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

Therapeutic Uses

This disclosure relates to compositions for use in managing respiratory distress and related disorders. In certain embodiments, the disclosure relates to methods of treating or preventing respiratory distress comprising administering an effective amount of a pharmaceutical composition comprising an active pharmaceutical agent disclosed herein to a subject in need thereof. In certain embodiments, the disclosure contemplates the use of pharmaceutical agents that prevent a claudin to cause claudin-18 to dissociate from ZO-1. In certain embodiments, the pharmaceutical agents decrease the concentration of claudin-5 in cells and tissues of the lungs.

In one embodiment, compounds, compositions and methods of managing by treatment or prevention of respiratory disorders comprising administering peptide or agents as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non- allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In certain embodiments, the disclosure contemplates methods of treating or preventing respiratory distress comprising administering an effective amount of a pharmaceutical composition comprising a pharmaceutical agent disclosed herein to a subject in need thereof. In certain embodiments, the subject is diagnosed with alcoholic lung syndrome; acute respiratory distress syndrome; sepsis-associated lung disorders; bacterial and viral pneumonia; ventilator induced lung injury; bronchopulmonary dysplasia (BPD); asthma; bronchial, allergic, intrinsic, extrinsic or dust asthma; chronic or inveterate asthma; late asthma or airways hyper-responsiveness; chronic obstructive pulmonary disease (COPD); bronchitis; emphysema; allergic rhinitis; or cystic fibrosis. In certain embodiments, the peptide or agent disclosed herein is administered in combination with another respiratory agent.

In certain embodiments, the subject is at risk of, exhibit symptoms of, or diagnosed with a respiratory distress, disease or condition.

In certain embodiments, the subject is an infant. In certain embodiments, the subject is suffering BPD. In certain embodiments, the subject is a premature infant. In certain embodiments, the subject is undergoing oxygen therapy as a protective agent.

In certain embodiments, the disclosure contemplates methods of treating or preventing BPD comprising administering comprising administering an effective amount of a pharmaceutical composition comprising a peptide or agent disclosed herein to a subject in need thereof. In certain embodiments, the subject is an infant suffering BPD or premature infants undergoing oxygen therapy as a protective agent.

In certain embodiments, the respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate; a p38 antagonist such as losmapimod; a phosphodiesterase (PDE) inhibitor such as a methylxanthanine, theophylline, and aminophylline; a selective PDE isoenzyme inhibitor, a PDE4 inhibitor and the isoform PDE4D, such as tetomilast, roflumilast, oglemilast, ibudilast, ronomilast; a modulator of chemokine receptor function such as vicriviroc, maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as setileuton, licofelone, quiflapon, zileuton, zafirlukast, or montelukast; and a myeloperoxidase antagonist such as resveratrol and piceatannol.

Methods of administering peptides and agents disclosed herein include, but are not limited to, pulmonary administration, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. In certain embodiments, the aerosolizing agent or propellant is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the disclosure contemplates oral administration.

Methods of administering peptides and agents disclosed herein include, but are not limited to, parenteral administration (e.g., intradermal, intramuscular, intraperitoneal, intravenous and subcutaneous), epidural, and mucosal (e.g., intranasal and oral routes). In a specific embodiment, the peptides or agents are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The peptides or agents of this disclosure may be administered in combination with other pharmaceutical agents such as antibiotics, anti-viral agents, anti-inflammatory agents, bronchodilators, or mucus-thinning medicines.

In certain embodiments, a bronchodilator for use as an additional therapeutic agent may be a short-acting beta2 agonist, a long-acting beta2 agonist or an anticholinergic. In some embodiments, the bronchodilator is any one of, or combination of, salbutamol/albuterol, levosalbutamol/levalbuterol, pirbuterol, epinephrine, ephedrine, terbutaline, salmeterol, clenbuterol, formoterol, bambuterol, indacaterol, theophylline, tiotropium, or ipratropium bromide.

In certain embodiments, an antibiotic for use as an additional therapeutic agent may be any antibiotic chosen by a physician for reducing lung infections in a subject. In some embodiments, the antibiotic is any one of, or combination of, xicillin, clavulanate potassium, aztreonam, ceftazidime, ciprofloxacin, gentamicin, or tobramycin.

Experiments

Certain experiments reported herein are also reported in Schlingmann et al. Nat Commun. 2016, 7:12276. Recitation of this reference is not an admission of prior art.

Chronic Alcohol Alters Lung Tight-Junction Permeability

The difference between AECs isolated from control- and alcohol-fed animals (alcohol-exposed AECs) was evaluated using two different measures of barrier function: transepithelial resistance (TER) and paracellular flux to soluble tracer molecules. Consistent with an increase in paracellular leak, alcohol-exposed AECs had significantly decreased TER and showed increased flux of both calcein (0.62 kDa) and Texas Red Dextran (10 kDa). Thus, alcohol exposure has a deleterious effect on AEC tight junctions.

As claudins are central to the regulation of tight-junction permeability, claudin protein composition of control- and alcohol-exposed AECs cultured on Transwell-permeable supports was examined by immunoblotting. The decrease in AEC barrier function induced by alcohol correlated with decreased claudin-4 protein (FIG. 1A). Claudin-1, claudin-3 and claudin-7 were unaffected. However, AEC-associated claudins did not simply decrease in response to alcohol. Instead, claudin-5 was significantly increased in alcohol-exposed AECs as compared with control AECs (FIG. 1A). There also was a trend towards increased claudin-18 in alcohol-exposed AECs as compared with control AECs (P=0.15, n=3, unpaired two-tailed t-test). As there was increased paracellular leak accompanying increased claudin-5 expression, we examined the effects of claudin remodelling in response to alcohol, to determine whether this had a destabilizing effect on tight junctions.

Increased Claudin-5 Causes Increased Paracellular Leak

Figure 1B:
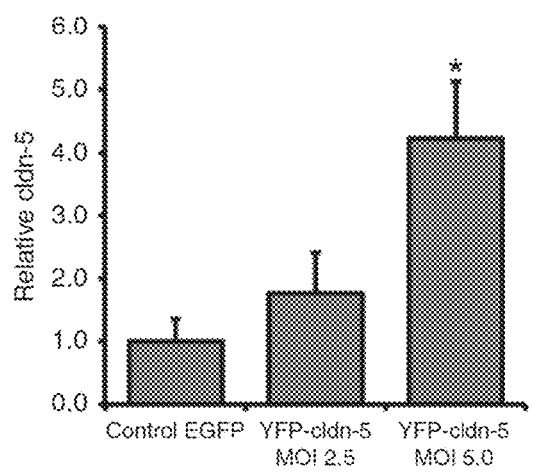
FIG. 1B shows data indicating yellow fluorescent protein (YFP)-claudin-5 at MOI of 5 significantly increased claudin-5 expression (n=3, *P=0.022, one way ANOVA with Tukey multiple comparisons test). Control AECs were transduced with adenovector YFP-claudin-5 at MOI of 2.5 or 5 or with EGFP adenovector at MOI of 5 as a control.
Figure 1C:
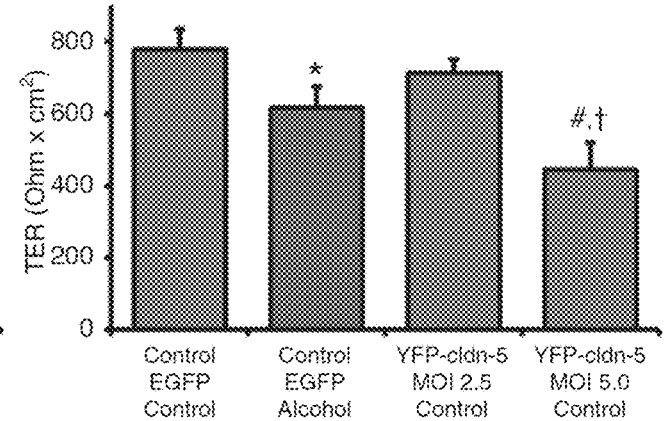
FIG. 1C shows data indicating decreased transepithelial resistance (TER). TER of alcohol exposed cells was significantly lower than comparable control cells (n=3, #P=0.0005 versus EGFP transduced control AECs; †P=0.028 versus EGFP transduced alcohol exposed cells, one way ANOVA, n=3, *P=0.036 control vs alcohol, one way ANOVA).

To confirm whether increased claudin-5 was sufficient to increase paracellular leak, the dose response of increased yellow fluorescent protein (YFP)-claudin-5 expression was examined using an adenovector to transduce primary AECs. A fourfold increase in claudin-5 expression ((YFP-claudin-5+claudin-5)/claudin-5) significantly decreased TER (FIGS. 1B and C) and increased paracellular flux. This level of YFP-claudin-5 expression is in the physiologic range, comparable to the increase in endogenous AEC claudin-5 expression induced by alcohol (FIG. 1A). In the converse experiment, lentiviral short hairpin RNA (shRNA) constructs were used to decrease claudin-5 expression.

```
Cldn-5 shRNA1 (Rat)
616-624
Sense
                                  (SEQ ID NO: 27)
5' (NheI) CCCCCCAACGGCGATT

ACGACAATTCAAGAGATTGTCGTAAT

CGCCGTTGGTTTTTGG (PacI) 3'

Anti
                                  (SEQ ID NO: 28)
5' (PacI) CCAAAAACCAACGGCG

ATTACGACAATCTCTTGAATTGTCGT

AATCGCCGTTGGGGGG (NheI) 3'

Cldn-5 shRNA2
1594-1612
sense
                                  (SEQ ID NO: 29)
5' (NheI) CCCCCCACCAAACTGC

CGCTAACTTCAAGAGAGTTAGCGGC

AGTTTGGTGGTTTTTGG (PacI) 3' anti
```

-continued

```
                                 (SEQ ID NO: 30)
5' (PacI) CCAAAAACCACCAAAC

TGCCGCTAACTCTCTTGAAGTTAGC

GGCAGTTTGGTGGGGGG (NheI) 3' scrambled
sense
                                 (SEQ ID NO: 31)
5' (NheI) CCCCAGTCATTGACGA

CAG CGTATTCAAGAGATACGCTGTC

GTCAATGACTTTTTTGG (PacI) 3' anti
                                 (SEQ ID NO: 32)
5' (PacI) CCAAAAAAGTCATTG

ACGACAGCGTATCTCTTGAATACGC

TGTCGTCAATGACTGGGG (NheI) 3'
```

As shown in FIGS. 1D and E, using shRNA to decrease claudin-5 expression by AECs from alcohol-fed rats caused a significant increase in TER and also decreased paracellular flux.

As claudin-4 decreased in response to dietary alcohol, it could also have a negative impact on AEC barrier function in combination with increased claudin-5. Thus, whether increased claudin-4 could rescue the effects of alcohol on AECs was examined. Alcohol-exposed AECs transduced with CFP-claudin-4 had only a partial increase in TER compared with control AECs. Moreover, the effects of increased claudin-4 were antagonized by a concurrent transduction with YFP-claudin-5. The fact that claudin-5 countered the ability of claudin-4 to promote paracellular barrier function suggests that these claudins are directly interacting. Formation of complexes containing native claudin-4 and native claudin-5 was confirmed by co-immunopurification analysis of AECs. Using co-immunopurification, it was observed that native claudin-5 directly interacts with native claudin-18 and ZO-1 indicating increased claudin-5 has a deleterious and dominant effect on other claudins and thereby impairs AEC barrier function.

Tight-Junction Spikes are Associated with Barrier Disruption

As revealed by immunofluorescence microscopy of claudin-18, AECs from alcohol-fed rats have changes in tight-junction morphology, most notably increased formation of tight-junction spikes (FIG. 2A), which are actin-associated structures perpendicular to the axis of the cell-cell interface that correlate with an increase in paracellular leak Normal AECs transduced to express increased claudin-5 also showed an increase in claudin-18 containing spikes, comparable to the effect of alcohol on tight-junction morphology (FIG. 2B). Morphologic disruption of tight junctions was not restricted to claudin-18, as claudin-5 and ZO-1 were also impaired in YFP-claudin-5-transduced AECs. To determine whether ZO-1 disruption was specifically linked to increased claudin-5, the effect of increased YFP-claudin-3 on ZO-1 localization by AECs was examined. It was found that there was little effect on tight-junction morphology based on localization of claudin-18 or ZO-1. In a complementary experiment, it was determined whether the ability of alcohol to induce formation of tight-junction spikes was antagonized by depleting claudin-5 using shRNA. As shown in FIG. 2C, this was the case for two different specific claudin-5 shRNAs. Thus, claudin-5 was sufficient to enhance formation of tight-junction spikes.

Although tight-junction spikes correlated with diminished paracellular barrier function, how spikes were mechanistically linked to paracellular leak was not known. It is hypothesized that spikes represented areas of enhanced tight-junction protein reorganization, which is known to increase paracellular leak. To address this, AECs expressing YFP-claudin-18 that were adjacent to untransfected AECs were used. It is noteworthy that YFP-claudin-18 acts to label tight-junction spikes in live cells and did not induce formation of spikes in a manner comparable to claudin-5. Spike-associated YFP-claudin-18 was internalized by neighboring non-transduced cells, suggesting that the adjacent cells internalized claudin-18 from neighboring cells. Moreover, co-localization of ZO-1 to YFP-claudin-18 was variable, as there were readily visualized YFP-claudin-18 structures that lacked co-localization with ZO-1, although claudin-18 and ZO-1 did co-localize in other spike-associated structures.

Figure 3A:
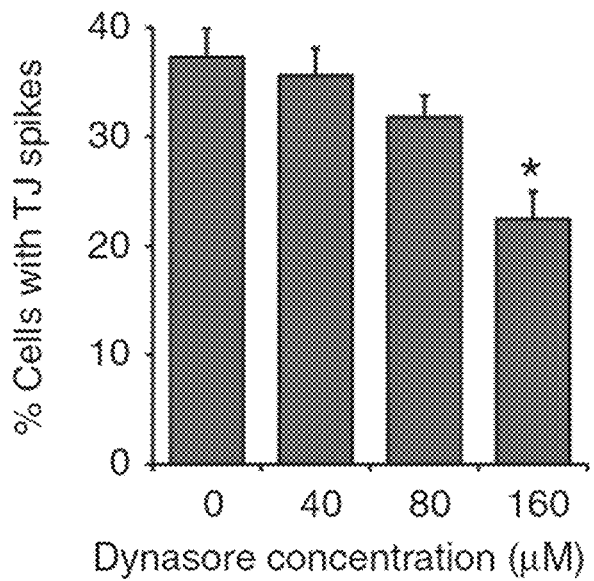
FIG. 3A shows data on the quantification of the % cells containing 3 or more tight junction spikes oriented towards the nucleus demonstrated that 160 µM Dynasore significantly decreased the number of cells from alcohol fed rats containing spikes (n=8-9 fields, *P=0.002, one way ANOVA with Tukey multiple comparisons test).
Figure 3B:
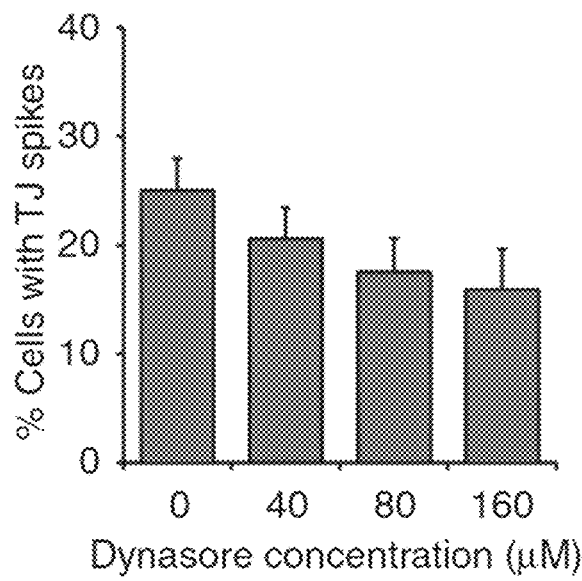
FIG. 3B shows data indicating Dynasore did not have a significant effect on spike formation by control cells n=8-9 fields, *P=0.002, one way ANOVA with Tukey multiple comparisons test).

To further characterize the behavior of claudins associated with tight-junction spikes, live-cell imaging microscopy of alcohol-exposed AECs transduced to express either YFP-claudin-5 or YFP-claudin-18 was used, which revealed the dynamic nature of tight-junction spikes. Specifically, claudin-labelled vesicles were found to both fuse with and bud from tight-junction spikes. To further confirm that spikes were sites of active claudin vesicle formation and fusion, the effects of the dynamin inhibitor Dynasore14 was examined on spike formation by alcohol-exposed AECs. Consistent with this, treatment with Dynasore at 160 µM for 4 h caused a significant decrease in the number of cells with tight-junction spikes (FIG. 3A) comparable to the number of cells containing spikes observed for untreated control AECs (FIG. 3B). Dynasore-treated cells also showed an increase in punctate YFP-claudin-18 labelling, which probably represents secretory and endocytic vesicles that are inhibited from fusing with target intracellular membranes by Dynasore. As an increase in tight-junction spikes correlated with decreased barrier function, these data suggest that increased vesicle-mediated trafficking of claudins both into and out of tight junctions contributes to paracellular leak in response to alcohol.

Claudin-5 Alters Interactions between Claudin-18 and ZO-1

As tight junctions are multi-protein complexes, paracellular barrier function requires coordinating heterologous interactions between tight-junction proteins. In intact cell junctions, protein-protein interactions are reflected by co-localization of two or more proteins in the same intracellular location when resolved at sufficient resolution. To understand how alcohol-induced changes affect tight junctions at a molecular level, AECs isolated from control- and alcohol-fed rats were examined by a form of super-resolution immunofluorescence microscopy, stochastic optical reconstruction microscopy (STORM), which has an X-Y resolution down to 20 nm. By the nature of the technique, STORM provides images that are composed of point densities, resulting in a particulate image at high magnification. STORM images obtained using the same labelling and imaging conditions appeared to have differences in the size of particulate clusters when comparing control versus alcohol-exposed AECs. Thus, the distribution of particulate clusters were quantified. STORM imaging of normal AECs showed that claudin-18, claudin-5 and ZO-1 clusters had median areas of 1,240, 1,410 and 1,590 nm$^2$, respectively. By contrast, alcohol-exposed AECs had claudin-18, claudin-5 and ZO-1 clusters with median areas of 1,410, 1,000 and 1,120 nm$^2$, respectively. The alcohol-induced decrease in median cluster size for claudin-5 and ZO-1 was significant, as determined by Mann-Whitney U-test; however, Claudin-18 cluster size was statistically unchanged. As these images were obtained using the same labelling and imaging conditions, the change in claudin-5 and ZO-1 cluster size induced by alcohol is likely to reflect tight-junction re-organization in response to alcohol, despite the inability to assign a specific physiologic correlate to particulate clusters.

STORM images of AEC tight junctions showed a predominant linear intercellular complex with some projections and limited meshwork architecture. Some images also showed tight-junction spikes. STORM analysis of AECs did not show an extensive meshwork, as tight junctions between adjacent type-I AECs in situ were shown to have a fairly limited architecture. Moreover, STORM images are obtained using the total internal reflection fluorescence mode of illumination and thus any junctional elements perpendicular to the narrow plane of focus would not be revealed using this approach. Here the STORM-imaging conditions were optimized for co-localization analysis between tight-junction proteins as opposed to maximizing imaging resolution.

Figure 4A:
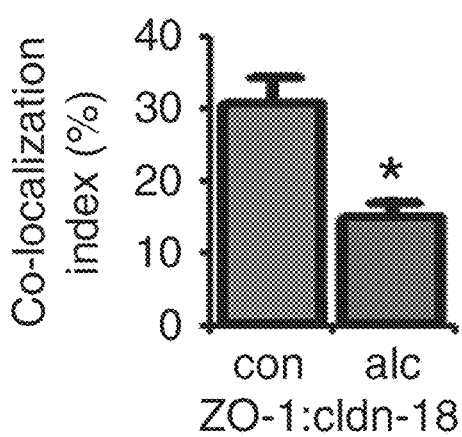
FIG. 4A shows data on the quantification of co-localization using stochastic optical reconstruction microscopy (STORM) images demonstrated a significant change. In alcohol-exposed AECs there was a significant decrease in ZO-1:claudin-18 (n=4 fields (control), n=3 fields (alcohol exposed AECs) *P=0.014, unpaired two-tailed t-test).
Figure 4B:
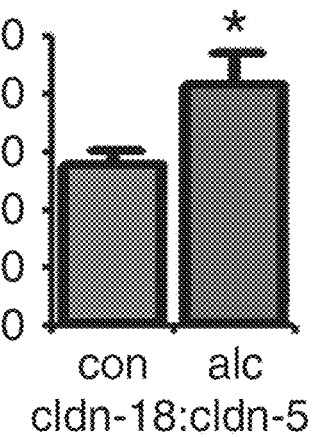
FIG. 4B shows data indicating a correlation with a significant increase in claudin-18:claudin-5 co-localization using STORM images (n=3 fields, *P=0.039, unpaired two-tailed t-test).
Figure 4C:
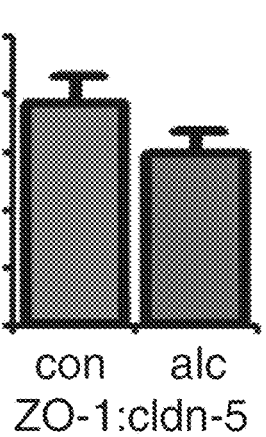
FIG. 4C shows data indicating ZO-1:claudin-5 co-localization was unchanged (n=4 fields, unpaired two-tailed t-test).

STORM enabled quantitative differences in co-localization to be measured, as these measurements were performed where cross-talk between the two different channels was minimized. In alcohol-exposed AECs, there was a significant decrease in co-localization between claudin-18 and ZO-1 as compared with control AECs (FIG. 4A). Conversely, there was an increase in co-localization between claudin-18 and claudin-5 in AECs isolated from alcohol-fed rats as compared with controls (FIG. 4B). This reciprocal relationship supports the hypothesis that in response to interacting with claudin-5, claudin-18 dissociates from ZO-1.

To further investigate the alcohol-induced changes in ZO-1:claudin-18 co-localization, AECs were examined using the PLA, which has a resolving power of 30-40 nm. PLA analysis of claudin-18 and ZO-1 in control AECs gave a robust signal. By contrast, alcohol-exposed AECs had a significantly diminished PLA signal (FIG. 5A). Conversely, claudin-18 and claudin-5 had a PLA signal that was increased in alcohol-exposed AECs as compared with control AECs (FIG. 5B). ZO-1:claudin-5 co-localization was comparable for control and alcohol-exposed AECs, although the PLA signals have a slightly different appearance, because the cluster size for both ZO-1 and claudin-5 is sensitive to alcohol. These results parallel our analysis of the effects of alcohol on claudin-18, claudin-5 and ZO-1 co-localization by STORM. Thus, two independent approaches demonstrate that ZO-1:claudin-18 proximity was diminished by alcohol and correlated with an increase in claudin-18:claudin-5 proximity.

To determine whether increased claudin-5 was sufficient to decrease association of claudin-18 and ZO-1, AECs transduced with YFP-claudin-5 was examined by STORM. As opposed to untransduced AECs, where the co-localization index between claudin-18 and ZO-1 was 30.5%, AECs expressing YFP-claudin-5 had significantly decreased co-localization between claudin-18 and ZO-1 that was comparable to alcohol-exposed AECs. The significant drop in co-localization between ZO-1 and claudin-18 is consistent with a decrease in interaction between these two proteins, which may alter the assembly state of claudin-18.

In AECs, both claudin-18 and ZO-1 are highly resistant to Triton X-100, suggesting that ZO-1:claudin-18 complexes are tightly associated with the cytoskeleton. Thus, the effects of increased claudin-5 on the extractability of claudin-18, claudin-5 and ZO-1 were examined by Triton X-100. Consistent with previous measurements, less than ~35% of claudin-18 can be solubilized by Triton X-100 under conditions where the insoluble fraction primarily reflects proteins incorporated into tight junctions 12 (FIG. 6A). By contrast, the majority of cell-associated claudin-5 is extractable by Triton X-100 (FIG. 6B).

When AECs were transduced with YFP-claudin-5, the Triton X-100 soluble pool of claudin-18 significantly increased from 35.2 to 42.1 representing a 20% increase in claudin-18 solubility (FIG. 6A). However, ZO-1 solubility was unchanged by increased claudin-5. Instead, the increase in claudin-18 solubility induced by YFP-claudin-5 expression (FIG. 6A) correlated with the decrease in co-localization between claudin-18 and ZO-1 from ~31% to ~16% as measured by STORM. This decrease in co-localization suggests that decreased ZO-1:claudin-18 interactions induced by increased claudin-5 are sufficient to destabilize the tight-junctional pool of claudin-18.

A claudin-5 Peptide Improves Alveolar Barrier Function

An acetylated D-amino acid peptide corresponding to the region of the second extracellular (E2) domain directly adjacent to the third transmembrane (TM3) domain of claudin-5, Ac-EFYDP(SEQ ID NO:1)-NH$_2$, was prepared. The E2/TM3 region is implicated in mediating cis-claudin interactions, based on the crystal structure of claudin-15, as well as functional studies of claudin-3:claudin-5 and homomeric claudin-5 interactions. In addition, the corresponding region of claudin-18, NFWMS (SEQ ID NO: 33) is not conserved and this region is sufficiently divergent from the corresponding DFYNP (SEQ ID NO: 34) sequence found in other major claudins found in the lung, including claudin-3, -4 and -7. Claudin-1 does have an EFYDP (SEQ ID NO: 1) motif; however, it is present at low levels in AECs.

Figures 7A, 7B:
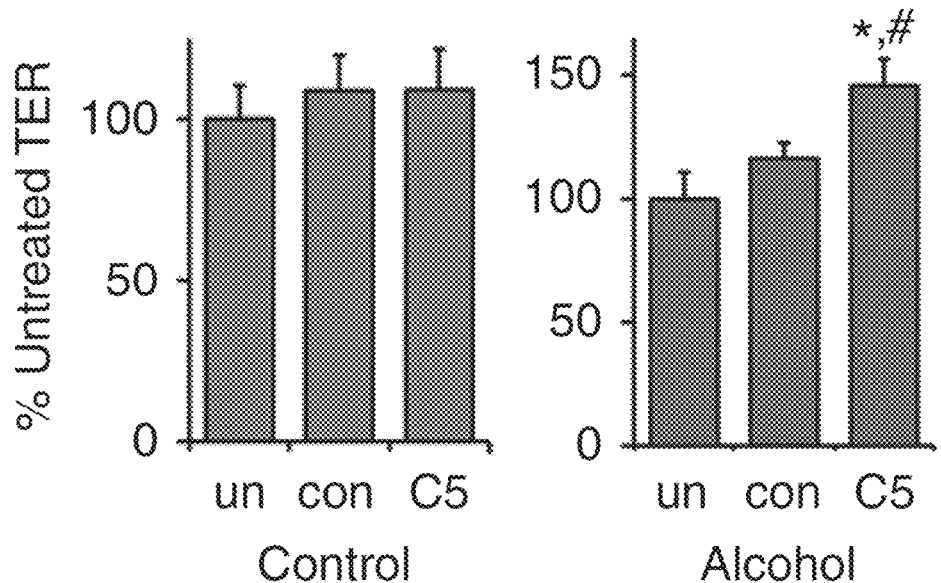
FIG. 7A shows data on TER for regular AECs in the presence of control Ac-LYQY(SEQ ID NO:35)-NH$_2$ and in the presence of Ac-EFYDP(SEQ ID NO:1)-NH$_2$ (C5). AECs isolated from control were cultured on Transwell permeable supports for 5 days and then either untreated (un), or incubated with 10 mM control peptide (con; Ac-LYQY(SEQ ID NO:35)-NH$_2$) or a claudin-5 extracellular domain mimetic peptide (C5; Ac-EFYDP(SEQ ID NO:1)-NH$_2$) for 16 h. The cells were examined for barrier function by transepithelial resistance (TER).
FIG. 7B shows data on TER for alcohol-exposed AECs in the presence of control Ac-LYQY(SEQ ID NO:35)-NH$_2$ and in the presence of Ac-EFYDP(SEQ ID NO:1)-NH$_2$ (C5) indicating that this claudin-5 extracellular domain mimetic increases barrier function of alcohol-exposed AECs (*P=0.014 versus untreated; #P=0.042 versus control; n=6, one way ANOVA with Tukey multiple comparisons test).
Figures 7C, 7D:
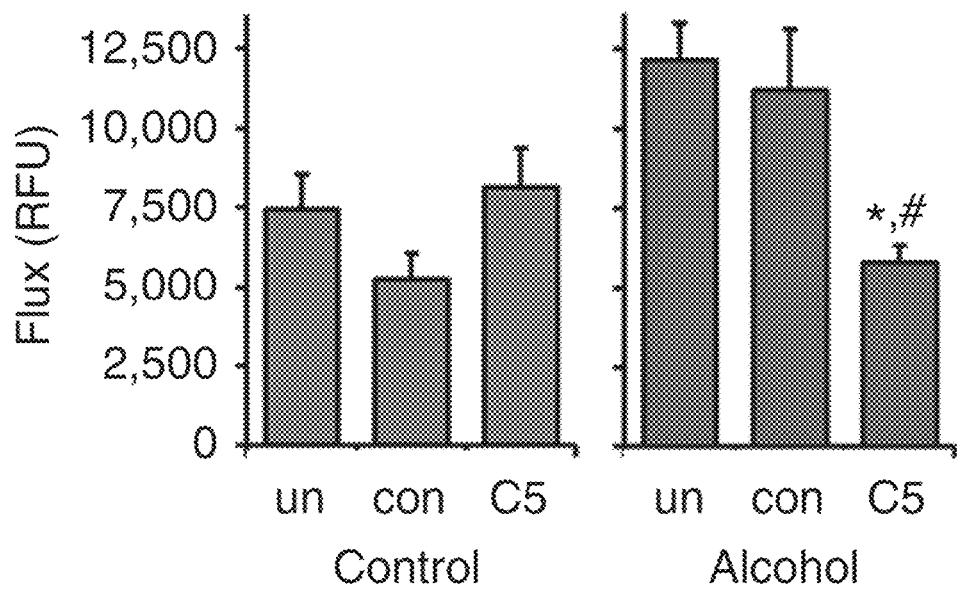
FIG. 7C shows data on paracellular flux of calcein for regular AECs in the presence of control Ac-LYQY(SEQ ID NO:35)-NH$_2$ and in the presence of Ac-EFYDP(SEQ ID NO:1)-NH$_2$ (C5).
FIG. 7D shows data on paracellular flux of calcein for alcohol-exposed AECs in the presence of control Ac-LYQY (SEQ ID NO:35)-NH$_2$ and in the presence of Ac-EFYDP (SEQ ID NO:1)-NH$_2$ (C5) (*P=0.007 versus untreated; #P=0.054 versus control; n=3, one way ANOVA with Tukey multiple comparisons test).
Figures 7E, 7F:
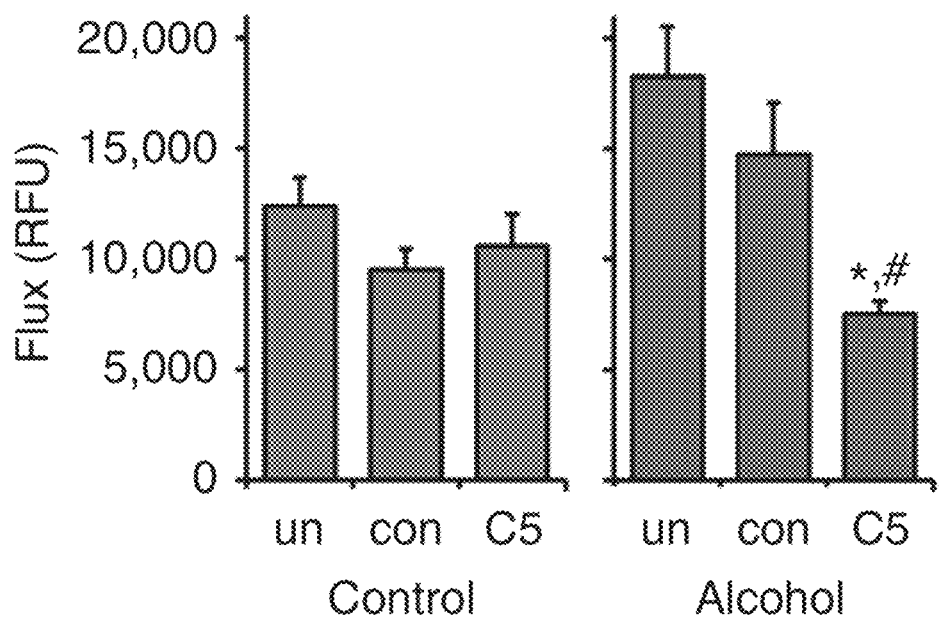
FIG. 7E shows data on paracellular flux of 10 kDa Texas Red dextran for regular AECs in the presence of control Ac-LYQY(SEQ ID NO:35)-NH$_2$ and in the presence of Ac-EFYDP(SEQ ID NO:1)-NH$_2$ (C5).
FIG. 7F shows data on paracellular flux of 10 kDa Texas Red dextran for alcohol-exposed AECs in the presence of control Ac-LYQY(SEQ ID NO:35)-NH$_2$ and in the presence of Ac-EFYDP(SEQ ID NO:1)-NH$_2$ (C5) (*P=0.009 versus untreated; #P=0.040 versus control; n=3, one way ANOVA with Tukey multiple comparisons test).
Figure 7G:
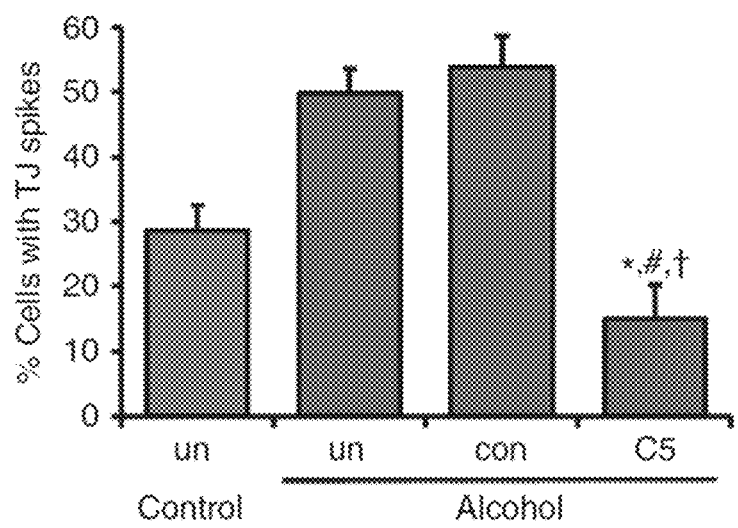
FIG. 7G shows data on cells from alcohol fed rats showed a decrease in tight junction spikes that was significantly less than that of untreated controls and alcoholic AECs that were either untreated or treated with a control peptide (*P<0.001 versus untreated; #P<0.001 versus control peptide; †P=0.041 versus untreated control AECs, n=9-11 fields from two independent experiments, one way ANOVA with Tukey multiple comparisons test).
Figure 7H:
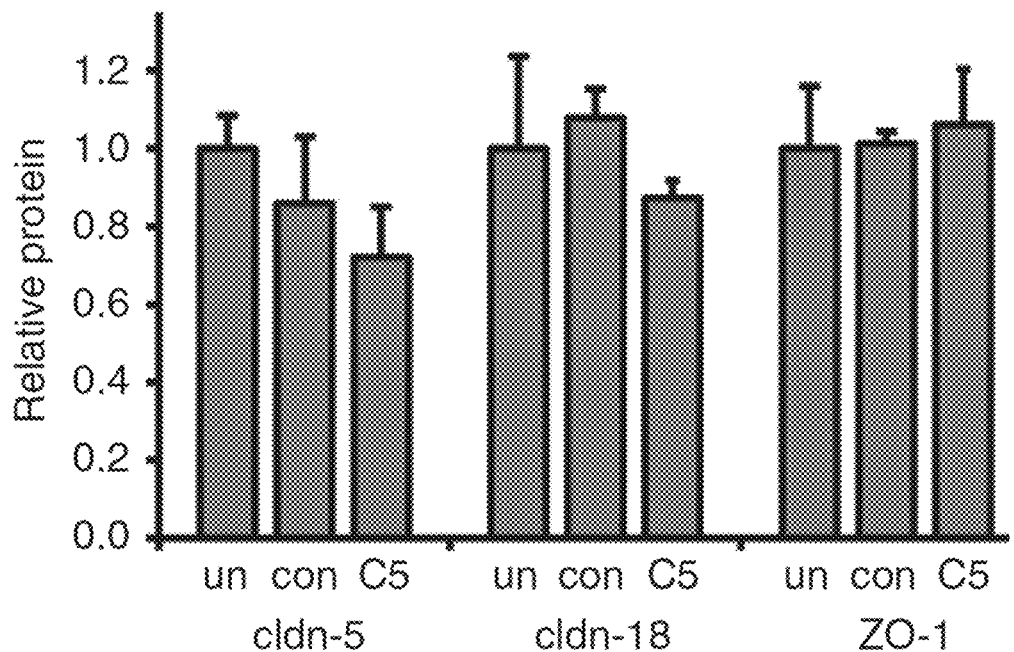
FIG. 7H shows data for control AECs were processed and examined by immunoblot for claudin-5, claudin-18 and ZO-1.
Figure 7I:
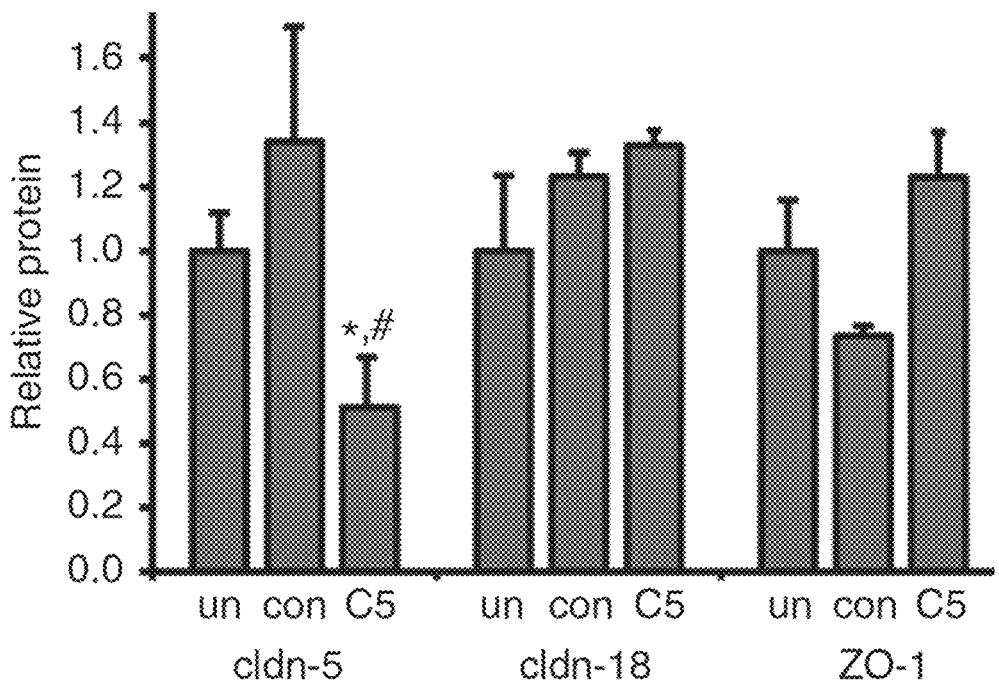
FIG. 7I shows data for alcohol-exposed AECs as treated above were processed and examined by immunoblot for claudin-5, claudin-18 and ZO-1. Cells from alcohol-fed rats that were treated with the C5 peptide showed a significant and specific decrease in claudin-5 (*P=0.042 versus untreated; #P=0.016 versus control; n=9, one way ANOVA with Tukey multiple comparisons test).

As shown in FIGS. 7B, D, and F, overnight incubation of alcohol-exposed AECs with the Ac-EFYDP(SEQ ID NO: 1)-NH$_2$ peptide increased barrier function, as measured by an increase in TER and decrease in paracellular flux of calcein and Texas Red Dextran. By contrast, control AECs were unaffected by the Ac-EFYDP(SEQ ID NO: 1)-NH$_2$ peptide (FIG. 7A, C, E). A control peptide, Ac-LYQY (SEQ ID NO:35)-NH$_2$, had no effect on AEC barrier function in either control or alcohol-exposed cells. The ability of Ac-EFYDP(SEQ ID NO: 1)-NH$_2$ to improve the barrier function of alcohol-exposed AECs correlated with a decrease in tight-junction spike formation (FIG. 7G) and a specific decrease in total claudin-5 content (FIG. 7I). Claudin-18 and ZO-1 were unaffected (FIG. 7I) as was claudin-1. These data provide an additional demonstration that an increase in endogenous claudin-5 diminishes AEC barrier function in response to alcohol indicating that targeting claudin-5 is a therapeutic approach to prevent alcoholic lung syndrome.

The invention claimed is:

1. A peptide consisting of SEQ ID NO: 1 (EFYDP), esters or salts thereof, wherein proline (P) is a D-isomer or an L-isomer, aspartic acid (D) is a D-isomer or an L-isomer, tyrosine (Y) is a D-isomer or an L-isomer, phenylalanine (F) is a D-isomer or an L-isomer, and glutamic acid (E) is a D-isomer or an L-isomer; and wherein glutamic acid (E) comprises an N-terminal alkanoyl group.

2. The peptide of claim 1 having the following formula,

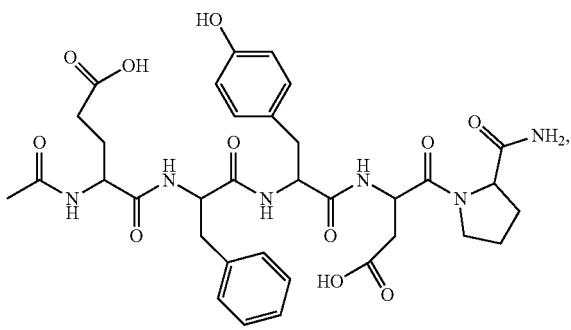 [SMILES: CC(=O)NC(CCC(=O)O)C(=O)NC(Cc1ccccc1)C(=O)NC(Cc1ccc(O)cc1)C(=O)NC(CC(=O)O)C(=O)N1CCCC1C(N)=O]

esters, or salts thereof.

3. The peptide of claim 1, wherein all of the amino acids are D-isomers.

4. A pharmaceutical composition comprising a peptide consisting of SEQ ID NO: 1 (EFYDP), esters or salts thereof and a pharmaceutically acceptable excipient to a subject in need thereof, wherein proline (P) is a D-isomer or an L-isomer, aspartic acid (D) is a D-isomer or an L-isomer, tyrosine (Y) is a D-isomer or an L-isomer, phenylalanine (F) is a D-isomer or an L-isomer, and glutamic acid (E) is a D-isomer or an L-isomer; and wherein glutamic acid (E) comprises an N-terminal alkanoyl group; and a pharmaceutically acceptable excipient.

5. The pharmaceutical composition of claim 4, wherein the peptide has the following formula,

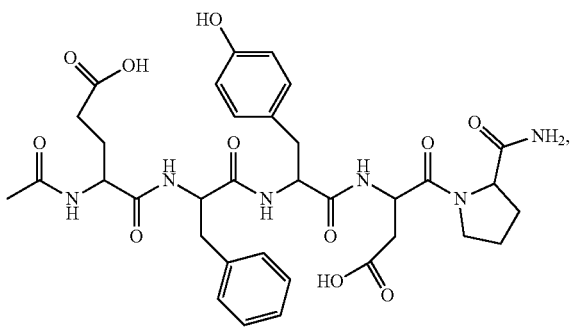 [SMILES: CC(=O)NC(CCC(=O)O)C(=O)NC(Cc1ccccc1)C(=O)NC(Cc1ccc(O)cc1)C(=O)NC(CC(=O)O)C(=O)N1CCCC1C(N)=O]

esters, or salts thereof.

6. The pharmaceutical composition of claim 5, wherein all of the amino acids are D-isomers.

7. The pharmaceutical composition of claim 4, wherein the pharmaceutically acceptable excipient is aerosolizing agent or a phospholipid.

8. The pharmaceutical composition of claim 7, wherein the aerosolizing agent is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof.

9. The pharmaceutical composition of claim 7, wherein the phospholipid is dipalmitoylphosphatidylcholine, palmitoyl-oleoyl phosphatidylglycerol, phosphatidylglycerol, or combinations thereof.

10. The pharmaceutical composition of claim 4, further comprising another respiratory agent.

11. The pharmaceutical composition of claim 10, wherein the respiratory agent is selected from triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, and alclometasone dipropionate.

12. The pharmaceutical composition of claim 10, wherein the respiratory agent is losmapimod.

13. The pharmaceutical composition of claim 10, wherein the respiratory agent is selected from theophylline and aminophylline.

14. The pharmaceutical composition of claim 10, wherein the respiratory agent is selected from tetomilast, roflumilast, oglemilast, ibudilast, and ronomilast.

15. The pharmaceutical composition of claim 10, wherein the respiratory agent is selected from vicriviroc, maraviroc, cenicriviroc, and navarixin.

16. The pharmaceutical composition of claim 10, wherein the respiratory agent is 4-hydroxy-1-methyl-3-octyloxy-7-sinapinoylamino-2(1H)-quinolinone.

17. The pharmaceutical composition of claim 10, wherein the respiratory agent is selected from setileuton, licofelone, quiflapon, zileuton, zafirlukast, and montelukast.

18. The pharmaceutical composition of claim 10, wherein the respiratory agent is selected from resveratrol and piceatannol.

* * * * *

SEQUENCE LISTING

<160> NUMBER OF SEQ ID NOS: 35

<210> SEQ ID NO 1
<211> LENGTH: 5
<212> TYPE: PRT
<213> ORGANISM: Artificial
<220> FEATURE:
<223> OTHER INFORMATION: Synthetic construct

<400> SEQUENCE: 1

Glu Phe Tyr Asp Pro
1               5

<210> SEQ ID NO 2
<211> LENGTH: 657
<212> TYPE: DNA
<213> ORGANISM: Homo sapiens

<400> SEQUENCE: 2
atggggtccg cagcgttgga gatcctgggc ctggtgctgt gcctggtggg ctgggggggt      60
ctgatcctgg cgtgcgggct gcccatgtgg caggtgaccg ccttcctgga ccacaacatc     120
gtgacggcgc agaccacctg aaggggctg tggatgtcgt gcgtggtgca gagcaccggg     180
cacatgcagt gcaaagtgta cgactcggtg ctggctctga gcaccgaggt gcaggcggcg     240
cgggcgctca ccgtgagcgc cgtgctgctg gcgttcgttg cgctcttcgt gaccctggcg     300
ggcgcgcagt gcaccacctg cgtggccccg ggcccggcca aggcgcgtgt ggccctcacg     360
ggaggcgtgc tctacctgtt ttgcgggctg ctggcgctcg tgccactctg ctggttcgcc     420
aacattgtcg tccgcgagtt ttacgacccg tctgtgcccg tgtcgcagaa gtacgagctg     480
ggcgcagcgc tgtacatcgg ctgggcggcc accgcgctgc tcatggtagg cggctgcctc     540
ttgtgctgcg cgcctgggt ctgcaccggc cgtcccgacc tcagcttccc cgtgaagtac     600
tcagcgccgc ggcggcccac ggccaccggc gactacgaca agaagaacta cgtctga     657

<210> SEQ ID NO 3
<211> LENGTH: 10
<212> TYPE: DNA
<213> ORGANISM: Artificial
<220> FEATURE:
<223> OTHER INFORMATION: Synthetic construct

<400> SEQUENCE: 3
tagttcttct                                                             10

<210> SEQ ID NO 4
<211> LENGTH: 7
<212> TYPE: DNA
<213> ORGANISM: Artificial
<220> FEATURE:
<223> OTHER INFORMATION: Synthetic construct

<400> SEQUENCE: 4 cggtggc                                                                7

<210> SEQ ID NO 5
<211> LENGTH: 8
<212> TYPE: DNA
<213> ORGANISM: Artificial
<220> FEATURE:
<223> OTHER INFORMATION: Synthetic construct

<400> SEQUENCE: 5

```
ggcgctga                                                              8
```

<210> SEQ ID NO 6
<211> LENGTH: 6
<212> TYPE: DNA
<213> ORGANISM: Artificial
<220> FEATURE:
<223> OTHER INFORMATION: Synthetic construct

<400> SEQUENCE: 6

```
ggaagc                                                                6
```

<210> SEQ ID NO 7
<211> LENGTH: 8
<212> TYPE: DNA
<213> ORGANISM: Artificial
<220> FEATURE:
<223> OTHER INFORMATION: Synthetic construct

<400> SEQUENCE: 7

```
gacggccg                                                              8
```

<210> SEQ ID NO 8
<211> LENGTH: 7
<212> TYPE: DNA
<213> ORGANISM: Artificial
<220> FEATURE:
<223> OTHER INFORMATION: Synthetic construct

<400> SEQUENCE: 8

```
gcagacc                                                               7
```

<210> SEQ ID NO 9
<211> LENGTH: 10
<212> TYPE: DNA
<213> ORGANISM: Artificial
<220> FEATURE:
<223> OTHER INFORMATION: Synthetic construct

<400> SEQUENCE: 9

```
acaagaggca                                                           10
```

<210> SEQ ID NO 10
<211> LENGTH: 9
<212> TYPE: DNA
<213> ORGANISM: Artificial
<220> FEATURE:
<223> OTHER INFORMATION: Synthetic construct

<400> SEQUENCE: 10

```
ccgcccagc                                                             9
```

<210> SEQ ID NO 11
<211> LENGTH: 7
<212> TYPE: DNA
<213> ORGANISM: Artificial
<220> FEATURE:
<223> OTHER INFORMATION: Synthetic construct

<400> SEQUENCE: 11

```
cgctgcg                                                               7
```

<210> SEQ ID NO 12
<211> LENGTH: 11
<212> TYPE: DNA
<213> ORGANISM: Artificial

```
<220> FEATURE:
<223> OTHER INFORMATION: Synthetic construct

<400> SEQUENCE: 12
acacgggcac a                                                              11

<210> SEQ ID NO 13
<211> LENGTH: 9
<212> TYPE: DNA
<213> ORGANISM: Artificial
<220> FEATURE:
<223> OTHER INFORMATION: Synthetic construct

<400> SEQUENCE: 13 acgacaatg                                                                  9

<210> SEQ ID NO 14
<211> LENGTH: 10
<212> TYPE: DNA
<213> ORGANISM: Artificial
<220> FEATURE:
<223> OTHER INFORMATION: Synthetic construct

<400> SEQUENCE: 14
agcagcccgc                                                                10

<210> SEQ ID NO 15
<211> LENGTH: 12
<212> TYPE: DNA
<213> ORGANISM: Artificial
<220> FEATURE:
<223> OTHER INFORMATION: Synthetic construct

<400> SEQUENCE: 15
gagggccaca cg                                                             12

<210> SEQ ID NO 16
<211> LENGTH: 9
<212> TYPE: DNA
<213> ORGANISM: Artificial
<220> FEATURE:
<223> OTHER INFORMATION: Synthetic construct

<400> SEQUENCE: 16 cgccttggc                                                                  9

<210> SEQ ID NO 17
<211> LENGTH: 11
<212> TYPE: DNA
<213> ORGANISM: Artificial
<220> FEATURE:
<223> OTHER INFORMATION: Synthetic construct

<400> SEQUENCE: 17
tgcactgcgc g                                                              11

<210> SEQ ID NO 18
<211> LENGTH: 9
<212> TYPE: DNA
<213> ORGANISM: Artificial
<220> FEATURE:
<223> OTHER INFORMATION: Synthetic construct

<400> SEQUENCE: 18 agggtcacg                                                                  9
```

<210> SEQ ID NO 19
<211> LENGTH: 7
<212> TYPE: DNA
<213> ORGANISM: Artificial
<220> FEATURE:
<223> OTHER INFORMATION: Synthetic construct

<400> SEQUENCE: 19 cacggcg                                                                 7

<210> SEQ ID NO 20
<211> LENGTH: 11
<212> TYPE: DNA
<213> ORGANISM: Artificial
<220> FEATURE:
<223> OTHER INFORMATION: Synthetic construct

<400> SEQUENCE: 20
gcctgcacct c                                                           11

<210> SEQ ID NO 21
<211> LENGTH: 11
<212> TYPE: DNA
<213> ORGANISM: Artificial
<220> FEATURE:
<223> OTHER INFORMATION: Synthetic construct

<400> SEQUENCE: 21
gagtcgtaca c                                                           11

<210> SEQ ID NO 22
<211> LENGTH: 11
<212> TYPE: DNA
<213> ORGANISM: Artificial
<220> FEATURE:
<223> OTHER INFORMATION: Synthetic construct

<400> SEQUENCE: 22
atgtgcccgg t                                                           11

<210> SEQ ID NO 23
<211> LENGTH: 14
<212> TYPE: DNA
<213> ORGANISM: Artificial
<220> FEATURE:
<223> OTHER INFORMATION: Synthetic construct

<400> SEQUENCE: 23
cacagcccct tcca                                                        14

<210> SEQ ID NO 24
<211> LENGTH: 12
<212> TYPE: DNA
<213> ORGANISM: Artificial
<220> FEATURE:
<223> OTHER INFORMATION: Synthetic construct

<400> SEQUENCE: 24
gcgccgtcac ga                                                            12

<210> SEQ ID NO 25
<211> LENGTH: 8
<212> TYPE: DNA
<213> ORGANISM: Artificial
<220> FEATURE:
<223> OTHER INFORMATION: Synthetic construct

<400> SEQUENCE: 25 tgccacat                                                                  8

<210> SEQ ID NO 26
<211> LENGTH: 11
<212> TYPE: DNA
<213> ORGANISM: Artificial
<220> FEATURE:
<223> OTHER INFORMATION: Synthetic construct

<400> SEQUENCE: 26
acgccaggat c                                                             11

<210> SEQ ID NO 27
<211> LENGTH: 58
<212> TYPE: DNA
<213> ORGANISM: Artificial
<220> FEATURE:
<223> OTHER INFORMATION: Synthetic construct

<400> SEQUENCE: 27 cccccccaacg gcgattacga caattcaaga gattgtcgta atcgccgttg gttttttgg        58

<210> SEQ ID NO 28
<211> LENGTH: 58
<212> TYPE: DNA
<213> ORGANISM: Artificial
<220> FEATURE:
<223> OTHER INFORMATION: Synthetic construct

<400> SEQUENCE: 28
ccaaaaacca acggcgatta cgacaatctc ttgaattgtc gtaatcgccg ttgggggg          58

<210> SEQ ID NO 29
<211> LENGTH: 58
<212> TYPE: DNA
<213> ORGANISM: Artificial
<220> FEATURE:
<223> OTHER INFORMATION: Synthetic construct

<400> SEQUENCE: 29 cccccccacca aactgccgct aacttcaaga gagttagcgg cagtttggtg gttttttgg        58

<210> SEQ ID NO 30
<211> LENGTH: 58

```
<212> TYPE: DNA
<213> ORGANISM: Artificial
<220> FEATURE:
<223> OTHER INFORMATION: Synthetic construct

<400> SEQUENCE: 30
ccaaaaacca ccaaactgcc gctaactctc ttgaagttag cggcagtttg gtgggggg      58

<210> SEQ ID NO 31
<211> LENGTH: 58
<212> TYPE: DNA
<213> ORGANISM: Artificial
<220> FEATURE:
<223> OTHER INFORMATION: Synthetic construct

<400> SEQUENCE: 31
ccccagtcat tgacgacagc gtattcaaga gatacgctgt cgtcaatgac tttttttgg     58

<210> SEQ ID NO 32
<211> LENGTH: 58
<212> TYPE: DNA
<213> ORGANISM: Artificial
<220> FEATURE:
<223> OTHER INFORMATION: Synthetic construct

<400> SEQUENCE: 32 ccaaaaagt cattgacgac agcgtatctc ttgaatacgc tgtcgtcaat gactgggg       58

<210> SEQ ID NO 33
<211> LENGTH: 5
<212> TYPE: PRT
<213> ORGANISM: Artificial
<220> FEATURE:
<223> OTHER INFORMATION: Synthetic construct

<400> SEQUENCE: 33

Asn Phe Trp Met Ser
1               5

<210> SEQ ID NO 34
<211> LENGTH: 5
<212> TYPE: PRT
<213> ORGANISM: Artificial
<220> FEATURE:
<223> OTHER INFORMATION: Synthetic construct

<400> SEQUENCE: 34

Asp Phe Tyr Asn Pro
1               5

<210> SEQ ID NO 35
<211> LENGTH: 4
<212> TYPE: PRT
<213> ORGANISM: Artificial
<220> FEATURE:
<223> OTHER INFORMATION: Synthetic construct

<400> SEQUENCE: 35

Leu Tyr Gln Tyr
1
```